United States Patent [19]

Naya et al.

[11] Patent Number: 5,917,608
[45] Date of Patent: Jun. 29, 1999

[54] SURFACE PLASMON SENSOR

[75] Inventors: Masayuki Naya; Taizo Akimoto, both of Kanagawa-ken, Japan

[73] Assignee: Fuji Photo Film Co., Ltd., Kanagawa-ken, Japan

[21] Appl. No.: 09/069,119

[22] Filed: Apr. 29, 1998

Related U.S. Application Data

[62] Division of application No. 08/841,620, Apr. 30, 1997.

[30] Foreign Application Priority Data

| Apr. 30, 1996 | [JP] | Japan | 8-109398 |
| May 15, 1996 | [JP] | Japan | 8-119892 |
| Jun. 4, 1996 | [JP] | Japan | 8-141698 |
| Sep. 4, 1996 | [JP] | Japan | 8-233864 |
| Sep. 4, 1996 | [JP] | Japan | 8-233868 |

[51] Int. Cl.$^6$ ............................................. G01N 21/55
[52] U.S. Cl. ........................ 356/445; 356/344; 204/461; 422/82.05
[58] Field of Search .................... 356/445–448, 356/344; 436/515–516; 204/403, 461; 422/82.05, 82.09, 82.11, 68.1

[56] References Cited

U.S. PATENT DOCUMENTS

| 4,915,812 | 4/1990 | Parce et al. |
| 5,035,863 | 7/1991 | Finlan et al. |
| 5,543,018 | 8/1996 | Stevens et al. |

FOREIGN PATENT DOCUMENTS

| 62-90600 | 4/1987 | Japan |
| 62-220853 | 9/1987 | Japan |
| 269936 | 11/1990 | Japan | 356/344 |
| 6167443 | 6/1994 | Japan |

OTHER PUBLICATIONS

Lange et al "Infared . . . Interface" Vacuum vol. 33 No. 10–12 pp. 763–766, 1983.

"Wall–Induced Orientational Order of a Liquid Crystal in the Isotropic Phase–an Evanescent–Wave–Ellipsometry Study", Hsiung et al., Physical Review Letters, vol. 57, No. 24, Dec. 15, 1986, pp. 3065–3068.

*Primary Examiner*—K P Hantis
*Attorney, Agent, or Firm*—Sughrue, Mion, Zinn, Macpeak & Seas, PLLC

[57] ABSTRACT

A surface plasmon sensor comprises a prism, a metal film, which is formed on one surface of the prism and is brought into contact with a sample, and a light source for producing a light beam. An optical system causes the light beam to pass through the prism and to impinge upon an interface between the prism and the metal film such that various different angles of incidence may be obtained with respect to the interface. A photodetector detects an intensity of the light beam, which has been totally reflected from the interface, with respect to each of the various different angles of incidence. An electrode stands facing the metal film with a liquid sample intervening therebetween, and a DC voltage is applied across the electrode and the metal film. A substance contained in the liquid sample is thus analyzed quickly and with a high sensitivity.

6 Claims, 12 Drawing Sheets

SURFACE PLASMON SENSOR

This is a divisional of application Ser. No. 08/841,620 filed Apr. 30, 1997.

BACKGROUND OF THE INVENTION

1. Field of the Invention

This invention relates to a surface plasmon sensor for quantitatively analyzing a substance in a sample by utilizing the occurrence of surface plasmon. This invention also relates to an evanescent ellipsosensor, wherein a light beam impinging upon a prism is totally reflected from an interface between the prism and a sample, a change in condition of polarization of the light beam due to the total reflection is detected, and a substance in the sample is thereby analyzed. This invention further relates to an electrophoresis sensor for analyzing a substance in a sample by utilizing electrophoresis.

2. Description of the Prior Art

In metals, free electrons vibrate collectively, and a compression wave referred to as a plasma wave is thereby produced. The compression wave occurring on the metal surface and having been quantized is referred to as the surface plasmon.

Various surface plasmon sensors for quantitatively analyzing a substance in a sample by utilizing a phenomenon, in which the surface plasmon is excited by a light wave, have heretofore been proposed. As one of well known surface plasmon sensors, a surface plasmon sensor utilizing a system referred to as the Kretschman arrangement may be mentioned. The surface plasmon sensor utilizing the system referred to as the Kretschman arrangement is described in, for example, Japanese Unexamined Patent Publication No. 6(1994)-167443.

Basically, the surface plasmon sensor utilizing the system referred to as the Kretschman arrangement comprises (i) a prism, (ii) a metal film, which is formed on one surface of the prism and is brought into contact with a sample, (iii) a light source for producing a light beam, (iv) an optical system for causing the light beam to pass through the prism and to impinge upon the interface between the prism and the metal film such that various different angles of incidence may be obtained with respect to the interface, and (v) a photo detecting means capable of detecting the intensity of the light beam, which has been totally reflected from the interface, with respect to each of the various different angles of incidence.

In order for various different angles of incidence to be obtained, a light beam having a comparatively small beam diameter may be deflected and caused to impinge upon the interface. Alternatively, a light beam having a comparatively large beam diameter may be converged on the interface such that the light beam may contain components, which impinge at various different angles of incidence upon the interface. In the former case, the light beam, which comes from the interface at various different angles of exit in accordance with the deflection of the incident light beam, may be detected with a small photodetector, which moves in synchronization with the deflection of the light beam, or may be detected with an area sensor extending in the direction, along which the angle of exit of the light beam changes. In the latter case, the light beam may be detected with an area sensor extending in a direction such that the area sensor can receive all of the light beam components coming from the interface at various different angles of exit.

With the surface plasmon sensor having the aforesaid constitution, when a light beam composed of a P-polarized light component (i.e., a polarized light component normal to the reflection interface) impinges at a specific angle of incidence $\theta_{SP}$, which is not smaller than the total reflection angle, upon the metal film, an evanescent wave having an electric field distribution occurs in the sample, which is in contact with the metal film, and the surface plasmon is excited at the interface between the metal film and the sample by the evanescent wave. In cases where the wave vector of the evanescent wave coincides with the wave number of the surface plasmon and wave number matching is obtained, the evanescent wave and the surface plasmon resonate, and energy of the light transfers to the surface plasmon. As a result, the intensity of the light, which is totally reflected from the interface between the prism and the metal film, becomes markedly low.

If the wave number of the surface plasmon is found from the specific angle of incidence $\theta_{SP}$, at which the aforesaid phenomenon occurs, a dielectric constant of the sample can be calculated. Specifically, the formula shown below obtains.

$$K_{SP}(\omega) = \frac{\omega}{c} \sqrt{\frac{\varepsilon_m(\omega)\varepsilon_s}{\varepsilon_m(\omega) + \varepsilon_s}}$$

wherein $K_{SP}$ represents the wave number of the surface plasmon, $\omega$ represents the angular frequency of the surface plasmon, $c$ represents the light velocity in a vacuum, $\varepsilon_m$ represents the dielectric constant of the metal, and $\varepsilon_s$ represents the dielectric constant of the sample.

If the dielectric constant $\varepsilon_s$ of the sample is found, the concentration of a specific substance contained in the sample can be calculated from a predetermined calibration curve, or the like. Therefore, the specific substance contained in the sample can be quantitatively analyzed by finding the specific angle of incidence $\theta_{SP}$, at which the intensity of the reflected light beam becomes low.

However, with the conventional surface plasmon sensors described above, the problems are encountered in that, when the substance contained in a trace amount in the liquid sample is analyzed, the sensitivity with which the substance to be analyzed is detected cannot be kept high, and a long time is required to carry out the analysis.

Also, it has heretofore been known that, when a light beam traveling in a first medium is totally reflected by an interface between the first medium and a second medium, which has a refractive index lower than the refractive index of the first medium, light referred to as the evanescent wave leaks to the second medium. When the light beam impinges upon the interface, the electric field of light changes in phase before the light beam is totally reflected from the interface and after the light beam is totally reflected from the interface. The change in phase varies for the P-polarized light component (normal to the reflection interface) and the S-polarized light component (parallel to the reflection interface). The change in the condition of polarization is inherent in accordance with the second medium which interacts with the evanescent wave.

Evanescent ellipsosensors for analyzing a substance contained in a sample by utilizing the phenomenon described above have heretofore been used. In the evanescent ellipsosensors, a constitution for totally reflecting a light beam from an interface between the sample and a prism is employed, and a technique (ellipsometry) for detecting a change in phase difference, i.e. a change in condition of polarization, is applied to the constitution. Such an evanescent ellipsosensor is described in, for example, PHYSICAL REVIEW LETTERS, Vol. 57, No. 24, Dec. 5, 1986, pp. 3065–3068. With the evanescent ellipsosensors, the prism is employed as the aforesaid first medium, the sample serving as the aforesaid second medium is brought into close contact with one surface of the prism, and the light beam is totally reflected from the interface between the prism and the sample. A change in condition of polarization due to the total reflection is detected, and physical properties or a total amount of the substance in the sample is thereby determined.

However, with the conventional evanescent ellipsosensors described above, the problems are encountered in that, when the substance contained in a trace amount in the liquid sample is analyzed, the sensitivity with which the substance to be analyzed is detected cannot be kept high, and a long time is required to carry out the analysis.

Further, electrophoresis apparatuses for analyzing substances contained in a sample by utilizing electrophoresis have heretofore been used. Such an electrophoresis apparatus is described in, for example, Japanese Unexamined Patent Publication No. 62(1987)-220853. Basically, with the electrophoresis apparatuses, a DC voltage is applied across an electrophoresis medium having been impregnated with a sample, and substances having electric charges, such as protein, protein decomposition products, nucleic acid, and nucleic acid decomposition products, which substances are contained in the sample, are thereby caused to migrate through the electrophoresis medium. The substances are thus separated spatially in the electrophoresis medium by the utilization of differences in migration speed among the substances.

In the conventional electrophoresis apparatuses, ordinarily, gel sheets constituted of a polyacrylamide gel, an agarose gel, or the like, are employed as the electrophoresis media. Also, ordinarily, in order for the spatially separated substances to be analyzed, techniques are employed wherein the substances in the sample are labeled with fluorescent substances, radioactive isotopes, and the like, and the positions of the labeled substances after migrating through the electrophoresis medium are recorded on a photographic material, a stimulable phosphor sheet described in Japanese Unexamined Patent Publication No. 62(1987)-90600, or the like.

However, in order for the positions of the labeled substances to be recorded, it is necessary to carry out exposure of the photographic material, the stimulable phosphor sheet, or the like, development of a latent image on the photographic material, a process for reading out image information having been recorded on the stimulable phosphor sheet, and the like. Therefore, with the conventional electrophoresis apparatus, considerable time and labor are required to analyze the samples. Also, considerable time and labor are required to label the substances in the sample with radioactive isotopes, or the like. Further, there is the risk that the labeling operation adversely affect the human body.

SUMMARY OF THE INVENTION

The primary object of the present invention is to provide a surface plasmon sensor, with which a substance contained in a liquid sample is analyzed quickly and with a high sensitivity.

Another object of the present invention is to provide a surface plasmon sensor, wherein multiple reflection interference of light does not occur, and the size of an optical system is kept small.

A further object of the present invention is to provide an evanescent ellipsosensor, with which a substance contained in a liquid sample is analyzed quickly and with a high sensitivity.

A still further object of the present invention is to provide an electrophoresis sensor, wherein complicated operation and process need not be carried out, and a substance contained in a sample is analyzed simply.

The present invention provides a first surface plasmon sensor, comprising:

i) a prism, ii) a metal film, which is formed on one surface of the prism and is brought into contact with a sample, iii) a light source for producing a light beam, iv) an optical system for causing the light beam to pass through the prism and to impinge upon an interface between the prism and the metal film such that various different angles of incidence may be obtained with respect to the interface, and v) a photo detecting means capable of detecting an intensity of the light beam, which has been totally reflected from the interface, with respect to each of the various different angles of incidence, wherein the improvement comprises the provision of:

a) an electrode, which stands facing the metal film with a liquid sample intervening therebetween, and b) means for applying a DC voltage across the electrode and the metal film.

The first surface plasmon sensor in accordance with the present invention may be modified such that the sample analysis can also be carried out on the side of the electrode which is provided for voltage application. Specifically, the present invention also provides a second surface plasmon sensor, wherein the aforesaid first surface plasmon sensor in accordance with the present invention is modified such that it may further comprise:

a second prism, the electrode being formed on one surface of the second prism and constituted of a metal film, a second light source for producing a second light beam, a second optical system for causing the second light beam to pass through the second prism and to impinge upon an interface between the second prism and the electrode such that various different angles of incidence may be obtained with respect to the interface between the second prism and the electrode, and a second photo detecting means capable of detecting an intensity of the second light beam, which has been totally reflected from the interface between the second prism and the electrode, with respect to each of the various different angles of incidence.

The present invention further provides a third surface plasmon sensor wherein, in lieu of the electrode for voltage application being located such that it may stand facing the metal film as in the aforesaid first surface plasmon sensor in accordance with the present invention, the electrode for voltage application is located at a position spaced apart from the metal film on the one surface of the prism.

The present invention still further provides fourth, fifth, and sixth surface plasmon sensors wherein, in lieu of the metal film being brought into direct contact with the liquid sample as in the aforesaid first, second, and third surface plasmon sensors in accordance with the present invention, respectively, a sensor film, to which an antigen or an antibody capable of undergoing an antigen-antibody reaction with a substance to be analyzed, that is contained in a liquid sample, has been fixed, is formed on the metal film and is brought into contact with the liquid sample.

The present invention also provides a seventh surface plasmon sensor, comprising:

i) a substrate permeable to light, ii) a light source for producing a light beam, which impinges upon the substrate, iii) an optical system for causing the light beam to impinge upon the substrate, iv) a grating for entry of the light beam, which grating is formed at a portion of one surface of the substrate on the light beam incidence side, the grating diffracting the light beam and entering the light beam into the substrate, v) a sensor means, which is formed on the other surface of the substrate opposite to the one surface and is constituted of a metal film, that is brought into contact with a sample, vi) a grating for radiation of the light beam, which grating is formed at a different portion of the one surface of the substrate on the light beam incidence side, the grating diffracting the light beam, which has been reflected from an interface between the substrate and the sensor means, and radiating the light beam out of the substrate, and vii) a photo detecting means capable of detecting an intensity of the light beam, which has been radiated out of the substrate, whereby a wave number of a surface plasmon, which occurs at an interface between the sensor means and the sample, is specified from the intensity of the light beam having been detected by the photo detecting means, and a substance contained in the sample is analyzed quantitatively.

In the seventh surface plasmon sensor, the light beam having been produced by the light source is irradiated by the optical system to the substrate and is diffracted by the grating for entry of the light beam. The diffracted light beam passes through the substrate and impinges upon the interface between the sensor means and the substrate.

Also, in the seventh surface plasmon sensor, the substrate permeable to light may be constituted of, for example, a glass substrate. The substrate may be constituted of a single piece. Alternatively, the substrate may be constituted of a plurality of pieces. In the latter case, for example, the substrate may be constituted of a glass plate, on which the grating for entry of the light beam and the grating for radiation of the light beam are formed, and a glass plate, on which the sensor means is formed, the two glass plates being combined with each other with a refractive index matching liquid intervening therebetween.

The present invention further provides a first evanescent ellipsosensor, comprising:

i) a prism, ii) a transparent electrode, which is formed on one surface of the prism and is brought into contact with a liquid sample, iii) a beam irradiating system for irradiating a light beam, which has been polarized in a predetermined condition of polarization, from the side of the prism such that the light beam may be totally reflected from an interface between the liquid sample and the transparent electrode, iv) means for detecting a change in condition of polarization of the light beam due to the total reflection, v) an opposite electrode, which stands facing the transparent electrode with the liquid sample intervening therebetween, and vi) means for applying a DC voltage across the opposite electrode and the transparent electrode.

The first evanescent ellipsosensor in accordance with the present invention may be modified such that the sample analysis can also be carried out on the side of the opposite electrode which is provided for voltage application. Specifically, the present invention still further provides a second evanescent ellipsosensor, wherein the aforesaid first evanescent ellipsosensor in accordance with the present invention is modified such that it may further comprise:

a second prism, a second transparent electrode serving as the opposite electrode being formed on one surface of the second prism, a second beam irradiating system for irradiating a second light beam, which has been polarized in a predetermined condition of polarization, from the side of the second prism such that the second light beam may be totally reflected from an interface between the liquid sample and the second transparent electrode, and means for detecting a change in condition of polarization of the second light beam due to the total reflection.

The present invention also provides a first electrophoresis sensor, comprising:

i) an electrophoresis medium having been impregnated with a sample, ii) a first electrode, which is constituted of a metal film and is located such that it may be in contact with one end of the electrophoresis medium, iii) a second electrode, which is located on the side of the other end of the electrophoresis medium, iv) means for applying a DC voltage across the first electrode and the second electrode, the DC voltage causing a substance, which is to be detected and is contained in the sample, to migrate from the other end of the electrophoresis medium toward the one end thereof, v) a prism, which located such that it may be in contact with the first electrode from the side opposite to the one end of the electrophoresis medium, vi) a beam irradiating system for causing a light beam to pass through the prism and to impinge upon an interface between the prism and the first electrode such that various different angles of incidence may be obtained with respect to the interface, and vii) a photo detecting means capable of detecting an intensity of the light beam, which has been totally reflected from the interface, with respect to each of the various different angles of incidence.

The present invention further provides a second electrophoresis sensor, comprising:

i) an electrophoresis medium having been impregnated with a sample, ii) a first electrode, which is transparent and is located such that it may be in contact with one end of the electrophoresis medium, iii) a second electrode, which is located on the side of the other end of the electrophoresis medium, iv) means for applying a DC voltage across the first electrode and the second electrode, the DC voltage causing a substance, which is to be detected and is contained in the sample, to migrate from the other end of the electrophoresis medium toward the one end thereof, v) a prism, which located such that it may be in contact with the first electrode from the side opposite to the one end of the electrophoresis medium, vi) a beam irradiating system for irradiating a light beam, which has been polarized in a predetermined condition of polarization, from the side of the prism such that the light beam may be totally reflected from an interface between the prism and the first electrode, and vii) means for detecting a change in condition of polarization of the light beam due to the total reflection.

A third electrophoresis sensor in accordance with the present invention is designed for analyzing a sample containing a substance to be detected, which has been labeled with a fluorescent substance. Specifically, the present invention still further provides a third electrophoresis sensor, comprising:

i) an electrophoresis medium having been impregnated with a sample containing a substance, which is to be detected and has been labeled with a fluorescent substance, ii) a first electrode, which is transparent and is located such that it may be in contact with one end of the electrophoresis medium, iii) a second electrode, which is located on the side of the other end of the electrophoresis medium, iv) means for applying a DC voltage across the first electrode and the second electrode, the DC voltage causing the substance, which is to be detected and is contained in the sample, to migrate from the other end of the electrophoresis medium toward the one end thereof, v) a prism, which located such that it may be in contact with the first electrode from the side opposite to the one end of the electrophoresis medium, vi) a beam irradiating system for irradiating a light beam from the side of the prism such that the light beam may be totally reflected from an interface between the prism and the first electrode, and vii) means for detecting fluorescence, which is produced by the fluorescent substance when the fluorescent substance is excited with an evanescent wave having leaked from the interface.

With the first surface plasmon sensor in accordance with the present invention, the DC voltage is applied across the metal film and the electrode, which are located with the liquid sample intervening therebetween. Therefore, the substance to be analyzed, which has electric charges in the liquid sample, can be electro-deposited on the metal film. The polarity of the voltage may be selected in accordance with whether the substance to be analyzed is a cation or an anion, or the like.

Due to the electro-deposition, the concentration of the substance to be analyzed becomes high in the portion of the liquid sample, which portion is in contact with the metal film. As a result, the total reflection cancellation angle changes quickly and markedly. Therefore, the substance to be analyzed can be analyzed quickly and with a high sensitivity. In particular, in cases where a substance in a liquid sample is to be detected by the utilization of an antigen-antibody reaction, i.e. in cases where, for example, an antigen (or an antibody) is fixed to the metal film and an antibody (or an antigen), which is contained in the liquid sample and specifically adsorbs to the metal film, is to be detected, the antigen-antibody reaction is promoted by the increase in concentration of the substance to be analyzed, and therefore the effects described above can be obtained more markedly.

With the second surface plasmon sensor in accordance with the present invention, the electrode provided for voltage application is constituted of the metal film, and the prism, the light source, the optical system, and the photo detecting means are located also for the electrode provided for voltage application, such that a sample analysis can also be carried out on the side of this electrode. Therefore, a substance having positive electric charges in the liquid sample and a substance having negative electric charges in the liquid sample can be analyzed simultaneously.

With the third surface plasmon sensor in accordance with the present invention, the DC voltage is applied across the metal film and the electrode, which are formed at positions spaced apart from each other on one surface of the prism. Therefore, as in the first and second surface plasmon sensors in accordance with the present invention, the substance to be analyzed, which has electric charges in the liquid sample, can be electro-deposited on the metal film. By virtue of the effects of the electro-deposition, the substance to be analyzed, which is contained in the liquid sample, can be analyzed quickly and with a high sensitivity.

With the fourth, fifth, and sixth surface plasmon sensors in accordance with the present invention, the sensor film, to which an antigen or an antibody capable of undergoing an antigen-antibody reaction with a substance to be analyzed, that is contained in the liquid sample, has been fixed, is formed on the metal film. As a result, the substance to be analyzed, that is contained in the liquid sample, combines with the sensor film. Therefore, the physical properties in the vicinity of the sensor means, which is constituted of the sensor film and the metal film, change markedly. Accordingly, the sensitivity of the sensor system can be kept high, and the rate of the antigen-antibody reaction can be kept high.

With the seventh surface plasmon sensor in accordance with the present invention, light coupling to the sensor means is carried out with the grating for entry of the light beam and the grating for radiation of the light beam, which are formed on the substrate. Therefore, multiple reflection interference, which will occur when a prism is utilized for the coupling, can be prevented from occurring.

Also, with the seventh surface plasmon sensor in accordance with the present invention, wherein no prism is used and the light coupling section is located in the plane-parallel form, the size of the surface plasmon sensor can be kept small, and adjustment of the optical axis can be carried out easily.

With the first evanescent ellipsosensor in accordance with the present invention, the DC voltage is applied across the transparent electrode and the opposite electrode, which are located with the liquid sample intervening therebetween. Therefore, the substance to be analyzed, which has electric charges in the liquid sample, can be electro-deposited on the transparent electrode. The polarity of the voltage may be selected in accordance with whether the substance to be analyzed is a cation or an anion, or the like.

Due to the electro-deposition, the concentration of the substance to be analyzed becomes high in the portion of the liquid sample, which portion is in contact with the transparent electrode. Therefore, the substance to be analyzed can be analyzed with a high sensitivity. In particular, in cases where a substance in a liquid sample is to be detected by the utilization of an antigen-antibody reaction, i.e. in cases where, for example, an antigen (or an antibody) is fixed to the transparent electrode and an antibody (or an antigen), which is contained in the liquid sample and specifically adsorbs to the metal film, is to be detected, the antigen-antibody reaction is promoted by the increase in concentration of the substance, which is to be analyzed, in accordance with the law of mass action, and therefore an analysis can be made quickly and with a high sensitivity.

Also, with the first evanescent ellipsosensor in accordance with the present invention, the electrode for voltage application, which is formed on one surface of the prism, is a transparent electrode. Therefore, as in the conventional apparatus wherein the electrode is not formed, the evanescent wave leaks to the liquid sample. Accordingly, the sample analysis can be carried out without being obstructed by the electrode.

Such that the light beam may be reflected totally, it is necessary for the transparent electrode and the prism to be constituted of materials having refractive indexes higher than the refractive index of the liquid sample. Also, from the view point of preventing the reflection from the interface between the prism and the transparent electrode and multiple reflection interference in the transparent electrode film, the transparent electrode and the prism should preferably be constituted of materials having an identical refractive index.

Particularly, with the second evanescent ellipsosensor in accordance with the present invention, the opposite electrode is constituted of a transparent electrode, and the prism, the beam irradiating system, and the means for detecting a change in condition of polarization are located also for the opposite electrode, such that a sample analysis can also be carried out on the side of the opposite electrode. Therefore, a substance having positive electric charges in the liquid sample and a substance having negative electric charges in the liquid sample can be analyzed simultaneously.

With the first electrophoresis sensor in accordance with the present invention, when a light beam impinges at an angle of incidence, which is not smaller than the total reflection angle, upon the first electrode constituted of the metal film, an evanescent wave having an electric field distribution occurs in the sample, which is in contact with the first electrode, and the surface plasmon is excited at the interface between the metal film and the sample by the evanescent wave. When the angle of incidence becomes equal to a specific angle $\theta_{SP}$, the wave number of the evanescent wave and the wave number of the surface plasmon become equal to each other, and wave number matching is obtained. In this condition, energy of the light transfers to the surface plasmon. As a result, the intensity of the light, which is totally reflected from the interface between the prism and the first electrode, becomes markedly low. This phenomenon occurs only when the incident light is composed of the P-polarized light component (normal to the metal film).

Therefore, the specific substance contained in the sample can be quantitatively analyzed by finding the angle of incidence $\theta_{SP}$, at which the intensity of the reflected light beam becomes low.

With the first electrophoresis sensor in accordance with the present invention, in this manner, only the substance having arrived at the first electrode is detected. A plurality of substances contained in the sample arrive at the first electrode after different lengths of time due to a difference in migration speed. Therefore, the substances are temporally separated from one another and detected.

As described above, with the first electrophoresis sensor in accordance with the present invention, a plurality of substances contained in the sample are temporally separated from one another and detected. Therefore, exposure operations for recording the images of the substances by spatially separating them, development processes, and the like, need not be carried out, and the substances contained in the sample can be analyzed easily.

Also, with the first electrophoresis sensor in accordance with the present invention, the substance contained in the sample is analyzed in accordance with the intensity of the reflected light described above. Therefore, operations for labeling the substance in the sample need not be carried out, and the analysis operation can be kept simple.

Effects of the second electrophoresis sensor in accordance with the present invention will be described hereinbelow. As described above, when a light beam traveling in a first medium is totally reflected by an interface between the first medium and a second medium, which has a refractive index lower than the refractive index of the first medium, light referred to as the evanescent wave leaks to the second medium. When the polarized light beam impinges upon the interface, the condition of polarization (i.e., the difference in phase between the P-polarized light component and the S-polarized light component) changes before the light beam is totally reflected from the interface and after the light beam is totally reflected from the interface. The change in the condition of polarization is inherent in accordance with the second medium which interacts with the evanescent wave.

With the second electrophoresis sensor in accordance with the present invention, the prism serves as the first medium, and the first electrode and the substance having arrived at the first electrode serve as the second medium. Therefore, the substance in the sample can be analyzed quantitatively by detecting a change in condition of polarization of the light beam due to the total reflection. In this manner, with the second electrophoresis sensor in accordance with the present invention, only the substance having arrived at the first electrode is detected. Also, a plurality of substances contained in the sample arrive at the first electrode after different lengths of time due to a difference in migration speed. Therefore, the substances are temporally separated from one another and detected.

Also, with the second electrophoresis sensor in accordance with the present invention, wherein the first electrode is a transparent electrode, the evanescent wave leaks to the liquid sample, and therefore the sample analysis can be made without being obstructed by the first electrode.

As described above, with the second electrophoresis sensor in accordance with the present invention, a plurality of substances contained in the sample are temporally separated from one another and detected. Therefore, exposure operations for recording the images of the substances by spatially separating them, development processes, and the like, need not be carried out, and the substances contained in the sample can be analyzed easily.

Further, with the second electrophoresis sensor in accordance with the present invention, the substance contained in the sample is analyzed by detecting a change in condition of polarization. Therefore, operations for labeling the substance in the sample need not be carried out, and the analysis operation can be kept simple.

Effects of the third electrophoresis sensor in accordance with the present invention will be described hereinbelow. With the third electrophoresis sensor in accordance with the present invention, the light beam is totally reflected from the interface between the prism and the first electrode. At this time, an evanescent wave leaks from the interface to the sample. The fluorescent substance serving as the label is excited with the evanescent wave and produces the fluorescence. The fluorescence thus produced is detected. Therefore, the substance having arrived at the first electrode can be analyzed quantitatively in accordance with the fluorescence.

In this manner, with the third electrophoresis sensor in accordance with the present invention, only the substance having arrived at the first electrode is detected. Also, a plurality of substances contained in the sample arrive at the first electrode after different lengths of time due to a difference in migration speed. Therefore, the substances are temporally separated from one another and detected.

As described above, with the third electrophoresis sensor in accordance with the present invention, a plurality of substances contained in the sample are temporally separated from one another and detected. Therefore, exposure operations for recording the images of the substances by spatially separating them, development processes, and the like, need not be carried out, and the substances contained in the sample can be analyzed easily.

DESCRIPTION OF THE PREFERRED EMBODIMENTS

The present invention will hereinbelow be described in further detail with reference to the accompanying drawings.

Figure 1:
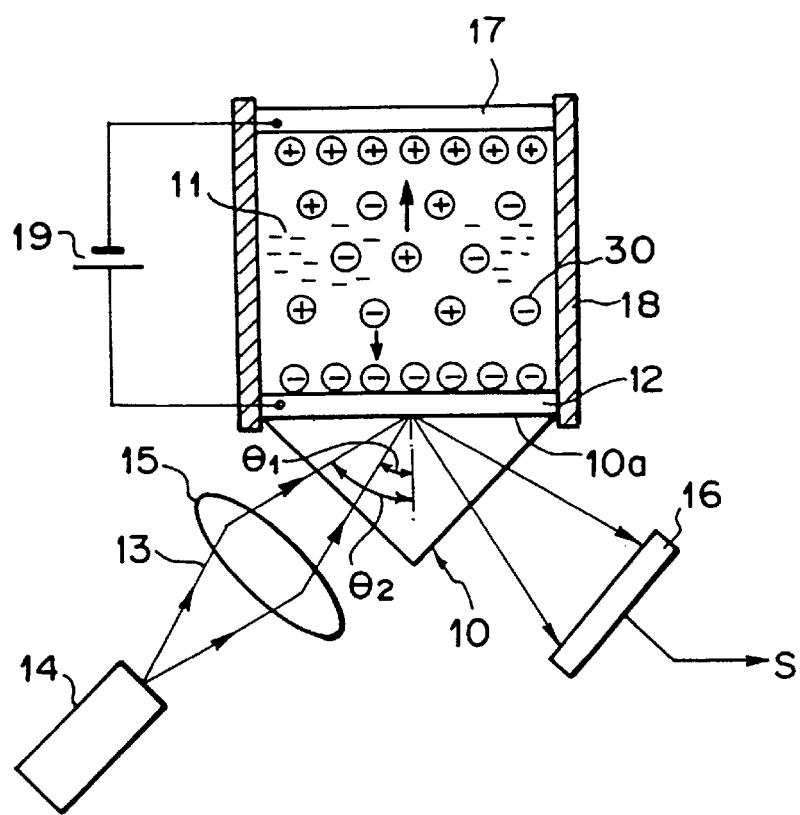
FIG. 1 is a side view showing a first embodiment of the surface plasmon sensor in accordance with the present invention.

FIG. 1 is a side view showing a first embodiment of the surface plasmon sensor in accordance with the present invention. As illustrated in FIG. 1, the surface plasmon sensor comprises a prism 10 having a triangular cross-section, and a metal film 12 constituted of gold, silver, or the like. The metal film 12 is formed on one surface (an upper surface in FIG. 1) of the prism 10 and is brought into contact with a liquid sample 11. The surface plasmon sensor also comprises a light source 14, which produces a light beam 13 and may be constituted of a semiconductor laser, or the like, and a cylindrical lens 15 for converging the light beam 13, which has been radiated in a divergent light condition from the light source 14, only in a plane normal to the major axis of the prism 10 (i.e., a plane parallel to the plane of the sheet of FIG. 1). The surface plasmon sensor further comprises a photo detecting means 16 for detecting an intensity of the light beam 13, which has been totally reflected from an interface 10a between the prism 10 and the metal film 12.

An electrode 17 is located at a position spaced an appropriate distance from the metal film 12 such that it may stand facing the metal film 12. The electrode 17 is supported by a tube-like support member 18 having its center axis extending vertically in FIG. 1. The periphery of the region sandwiched between the metal film 12 and the electrode 17 is closed by the support member 18. The metal film 12 and the electrode 17 are respectively connected to a positive pole and a negative pole of a DC power source 19.

The light beam 13 is converged in the manner described above by the action of the cylindrical lens 15. Therefore, as exemplified by the minimum angle of incidence $\theta_1$ and the maximum angle of incidence $\theta_2$ in FIG. 1, the light beam 13 contains components impinging at various different angles of incidence $\theta$ upon the interface 10a. The angles of incidence $\theta$ are set to be not smaller than the total reflection angle. As a result, the light beam 13 is totally reflected from the interface 10a, and the reflected light beam 13 contains the components, which have been reflected at various different angles of reflection.

As the photo detecting means 16, means having a light receiving section, which extends in the direction that is capable of receiving all of the components of the light beam 13 having been reflected at different angles of reflection in the manner described above, is employed. The photo detecting means 16 may be constituted of a charge coupled device (CCD) line sensor, or the like. A photo detection signal S is obtained from each of light receiving elements of the photo detecting means 16. Therefore, the photo detection signal S represents the intensity of the light beam 13 with respect to each of the various different angles of reflection (i.e., with respect to each of the various different angles of incidence).

How a sample analysis is carried out in the surface plasmon sensor having the constitution described above will be described hereinbelow. The region between the metal film 12 and the electrode 17 is filled with the liquid sample 11, which contains an anionic substance to be analyzed 30. Also, the DC power source 19 applies a DC voltage across the metal film 12 and the electrode 17. The light beam 13 is converged by the action of the cylindrical lens 15 in the manner described above and is irradiated toward the metal film 12. The light beam 13 is totally reflected from the interface 10a between the metal film 12 and the prism 10, and the reflected light beam 13 is detected by the photo detecting means 16.

Figure 2:
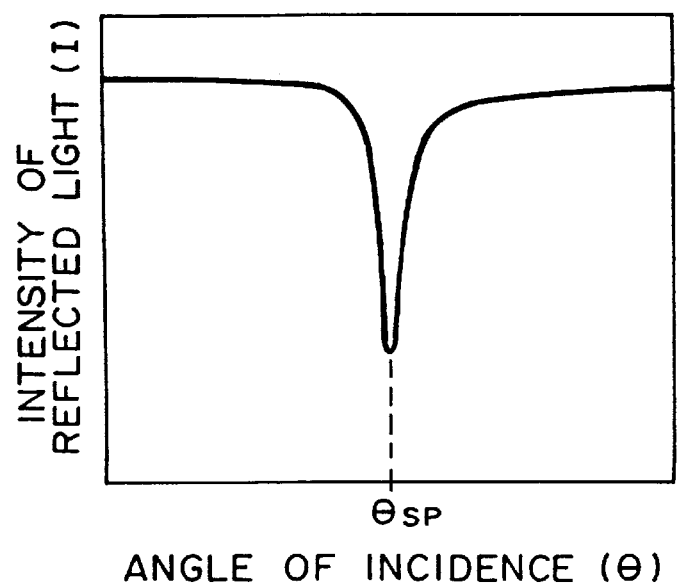
FIG. 2 is a graph showing approximate relationship between an angle of incidence of a light beam upon a reflection interface and an intensity of a totally reflected light in a surface plasmon sensor.

As described above, the photo detection signal S obtained from each of the light receiving elements of the photo detecting means 16 represents the intensity I of the totally reflected light beam 13 with respect to each of the angles of incidence θ. FIG. 2 approximately shows the relationship between the intensity I of the reflected light and the angles of incidence θ.

The light impinging at a specific angle of incidence $\theta_{SP}$ upon the interface 10a excites surface plasmon at an interface between the metal film 12 and the liquid sample 11. As for the light impinging at the specific angle of incidence $\theta_{SP}$ upon the interface 10a, the intensity I of the reflected light becomes markedly low. From the photo detection signal S obtained from each of the light receiving elements of the photo detecting means 16, the specific angle of incidence $\theta_{SP}$ can be determined. As described above in detail, the substance to be analyzed 30 contained in the liquid sample 11 can be analyzed quantitatively in accordance with the value of $\theta_{SP}$.

Also, since the DC voltage is applied across the metal film 12 and the electrode 17, which are connected to the DC power source 19, the anionic substance to be analyzed 30, which is contained in the liquid sample 11, is electro-deposited on the metal film 12. Therefore, the concentration of the substance to be analyzed 30 becomes high at the portion of the liquid sample 11, which portion is in contact with the metal film 12, and the substance to be analyzed 30 can be analyzed quickly and with a high sensitivity. As the anionic substance to be analyzed 30, an antigen (α-FP) dispersed in PBS, or the like, may be mentioned.

In cases where the substance to be analyzed 30, which is contained in the liquid sample 11, is detected by the utilization of an antigen-antibody reaction, it is often desired that the relationship between the intensity I of the reflected light and the angles of incidence θ can be detected on the real time basis as time passes while the antigen-antibody reaction is proceeding. With the first embodiment of the surface plasmon sensor in accordance with the present invention, wherein the substance to be analyzed 30 can be detected quickly as described above, the real time detection can be completed quickly.

In the first embodiment of the surface plasmon sensor in accordance with the present invention, in order for the various different angles of incidence θ to be obtained, the light beam 13 having a comparatively large beam diameter is irradiated such that it may be converged on the interface 10a. Alternatively, various different angles of incidence θ may be obtained by deflecting a light beam having a comparatively small beam diameter.

Figure 3:
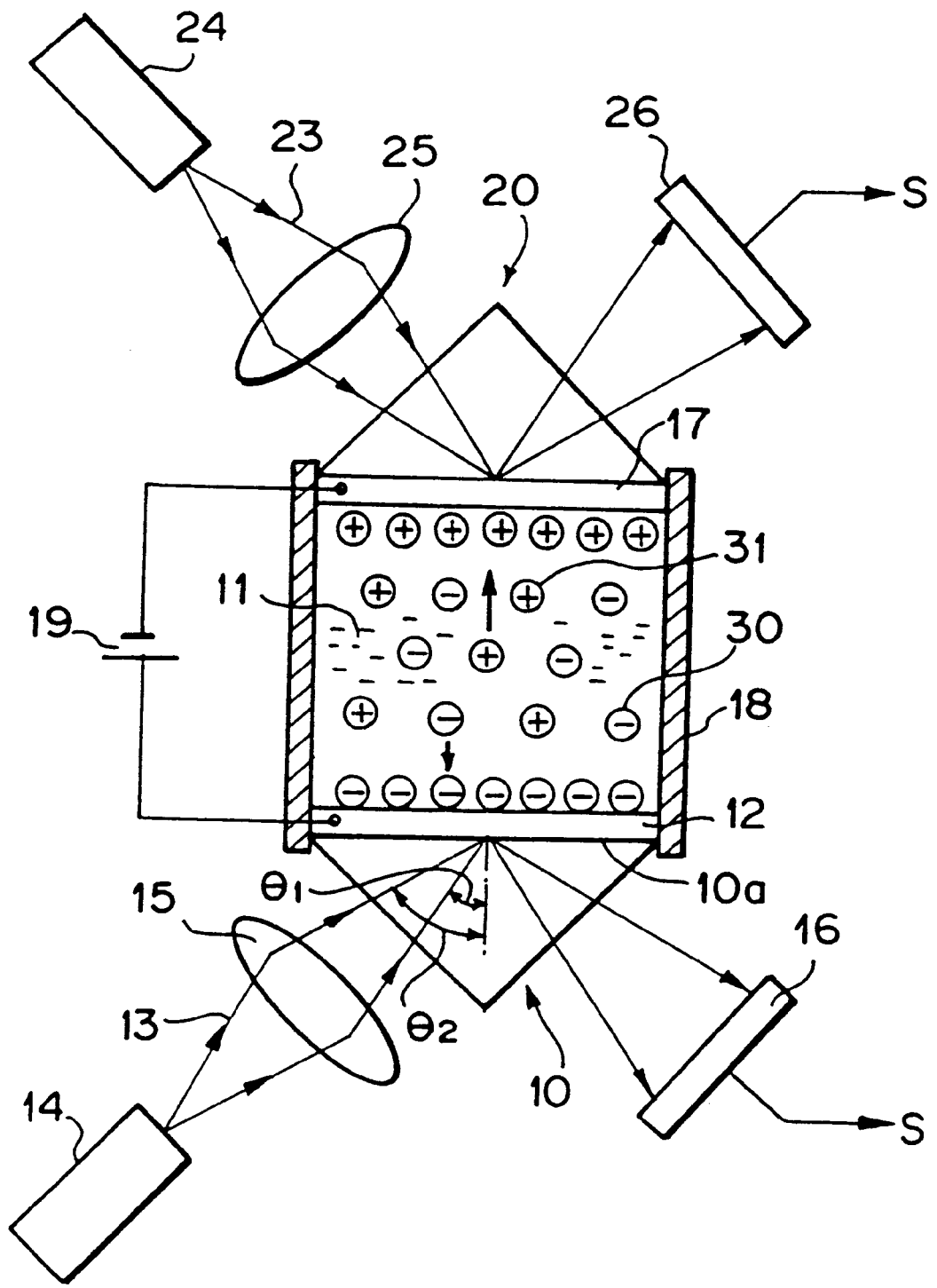
FIG. 3 is a side view showing a second embodiment of the surface plasmon sensor in accordance with the present invention.

A second embodiment of the surface plasmon sensor in accordance with the present invention will be described hereinbelow with reference to FIG. 3. In FIG. 3 and in FIGS. 4 to 8, similar elements are numbered with the same reference numerals with respect to FIG. 1.

The second embodiment of the surface plasmon sensor shown in FIG. 3 is basically similar to the first embodiment of FIG. 1, except that the second embodiment further comprises a second prism 20, a second light source 24 for producing a light beam 23, a second cylindrical lens 25, and a second photo detecting means 26. In this case, as the electrode 17, a film of a metal, such as gold or silver, is employed.

The elements newly added to the second embodiment of the surface plasmon sensor in accordance with the present invention constitute another surface plasmon sensor by utilizing the electrode 17, which is constituted of the metal film, in the same manner as that of the metal film 12. Specifically, the second prism 20, the second light source 24, the second cylindrical lens 25, and the second photo detecting means 26 respectively have the same actions as those of the prism 10, the light source 14, the cylindrical lens 15, and the photo detecting means 16.

In the second embodiment of FIG. 3, the analysis of the anionic substance to be analyzed 30, which is contained in the liquid sample 11, is carried out in the same manner as that described above. Also, in the second embodiment of FIG. 3, a cationic substance to be analyzed 31, which is contained in the liquid sample 11, is electro-deposited on the electrode 17. Therefore, with the second prism 20, the second light source 24, the second cylindrical lens 25, and the second photo detecting means 26, an analysis of the substance to be analyzed 31 can be carried out in the same manner.

In such cases, the concentration of the substance to be analyzed 31 becomes high at the portion of the liquid sample 11, which portion is in contact with the electrode 17, and the substance to be analyzed 31 can be analyzed quickly and with a high sensitivity.

Figure 4:
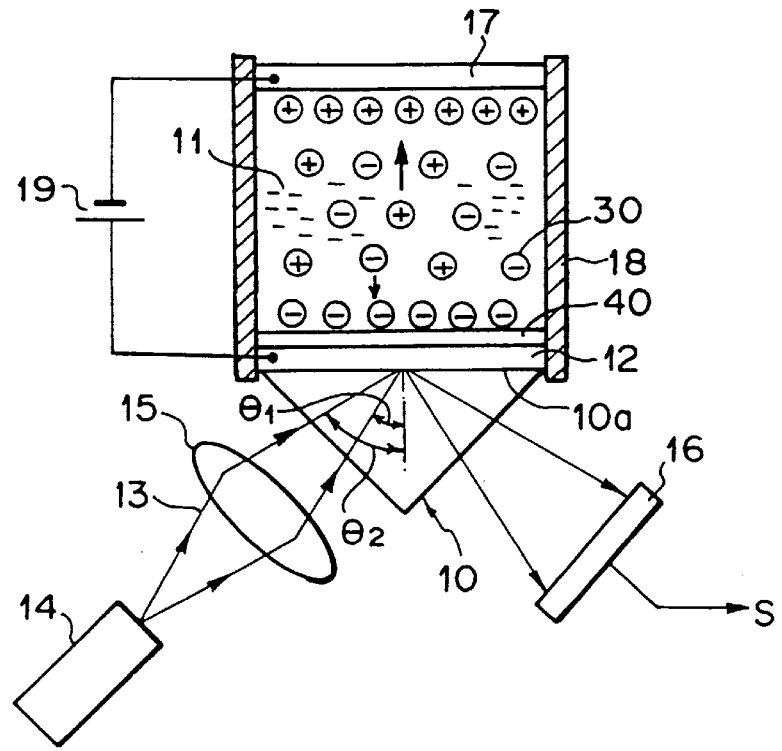
FIG. 4 is a side view showing a third embodiment of the surface plasmon sensor in accordance with the present invention.

A third embodiment of the surface plasmon sensor in accordance with the present invention will be described hereinbelow with reference to FIG. 4. The third embodiment of the surface plasmon sensor shown in FIG. 4 is basically similar to the first embodiment of FIG. 1, except that a sensor film 40 is formed on the metal film 12, and the liquid sample 11 is brought into direct contact with the sensor film 40. An antigen or an antibody capable of undergoing an antigen-antibody reaction with the substance to be analyzed 30, which is contained in the liquid sample 11, has been fixed to the sensor film 40. By way of example, in cases where the substance to be analyzed 30 is the aforesaid antigen (α-FP), IgG, or the like, may be employed as the antibody.

In the third embodiment of FIG. 4, the substance to be analyzed 30, which is contained in the liquid sample 11, is attracted toward the metal film 12 by the aforesaid electro-deposition effects and combines with the sensor film 40 by the antigen-antibody reaction. Therefore, the physical properties change markedly in the vicinity of the sensor section, which is constituted of the sensor film 40 and the metal film 12. Accordingly, the sensitivity of the sensor system can be kept high, and the rate of the antigen-antibody reaction can be kept high.

Figure 5:
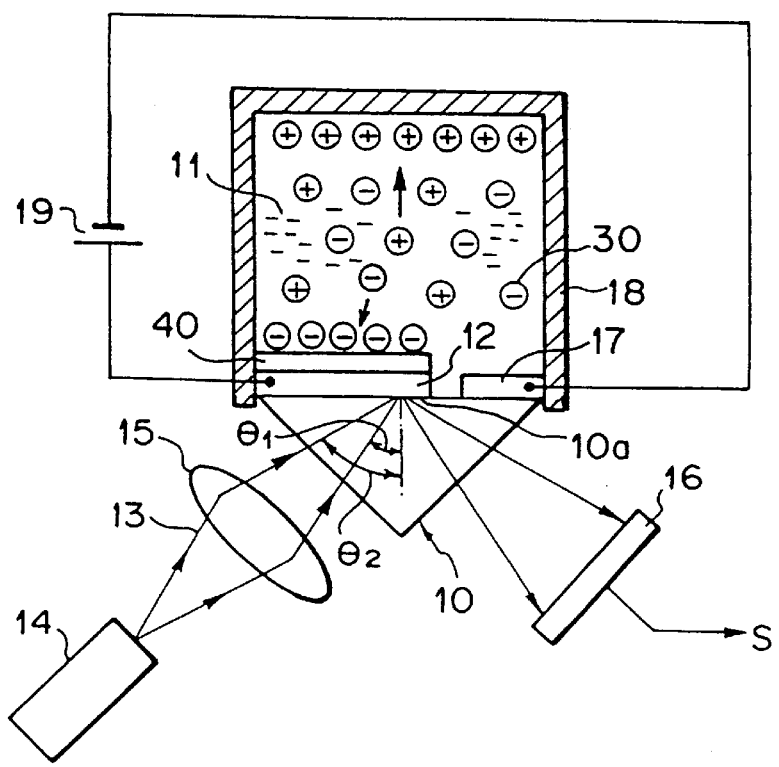
FIG. 5 is a side view showing a fourth embodiment of the surface plasmon sensor in accordance with the present invention.
Figure 6:
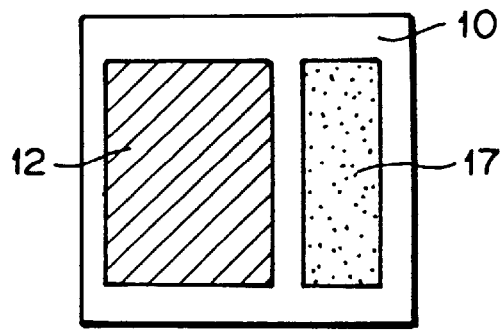
FIG. 6 is a plan view showing relationship between positions of a metal film and an electrode for voltage application in the fourth embodiment of the surface plasmon sensor shown in FIG. 5.

A fourth embodiment of the surface plasmon sensor in accordance with the present invention will be described hereinbelow with reference to FIG. 5. The fourth embodiment of the surface plasmon sensor shown in FIG. 5 is basically similar to the first embodiment of FIG. 1, except that, instead of the metal film 12 and the electrode 17 facing each other, the metal film 12 and the electrode 17 are located at positions spaced apart from each other on one surface of the prism 10. FIG. 6 is a plan view showing the relationship between the positions of the metal film 12 and the electrode 17 in the fourth embodiment of FIG. 5.

In the fourth embodiment of FIG. 5, when the DC power source 19 applies the DC voltage across the metal film 12 and the electrode 17, the anionic substance to be analyzed 30, which is contained in the liquid sample 11, is attracted toward the metal film 12 by the electro-deposition effects. Therefore, the concentration of the substance to be analyzed 30 becomes high at the portion of the liquid sample 11, which portion is close to the metal film 12, and the substance to be analyzed 30 can be analyzed quickly and with a high sensitivity.

In the fourth embodiment of FIG. 5, a sensor film 40, which is of the same type as that employed in the third embodiment of FIG. 4, is formed on the metal film 12. Therefore, in this embodiment, the physical properties change markedly in the vicinity of the sensor section, which is constituted of the sensor film 40 and the metal film 12. Accordingly, the sensitivity of the sensor system can be kept high, and the rate of the antigen-antibody reaction can be kept high.

Figure 7:
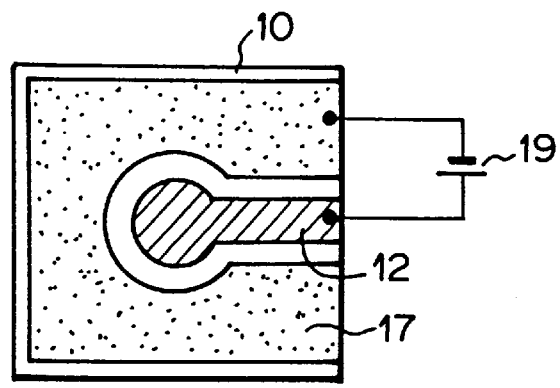
FIG. 7 is a plan view showing a different example of relationship between positions of a metal film and an electrode for voltage application in the surface plasmon sensor in accordance with the present invention.
Figure 8:
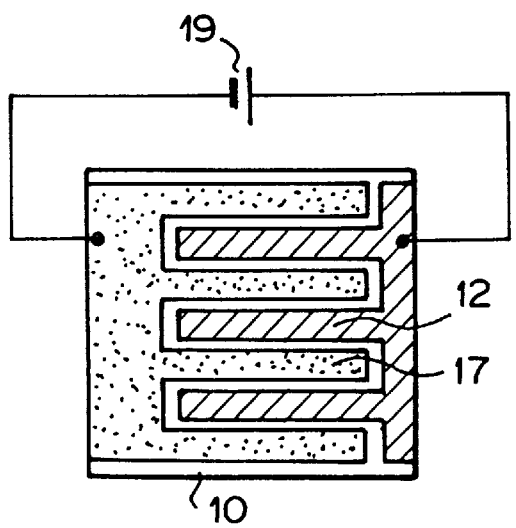
FIG. 8 is a plan view showing a further different example of relationship between positions of a metal film and an electrode for voltage application in the surface plasmon sensor in accordance with the present invention.

In cases where the metal film 12 and the electrode 17 are formed at positions spaced apart from each other on one surface of the prism 10 as in the fourth embodiment of FIG. 5, the shapes of the metal film 12 and the electrode 17 are not limited to those shown in FIG. 6 and may be designed as illustrated in, for example, FIGS. 7 and 8.

In cases where the shapes illustrated in FIG. 8 are employed, the so-called multi-channel constitution can be obtained. Specifically, in such cases, the substance to be analyzed 30, which is contained in the liquid sample 11, is attracted to each of the three comb teeth-like portions of the metal film 12. Therefore, three sensor sections can be obtained, and the analysis can be carried out simultaneously at the three sensor sections.

Figure 9:
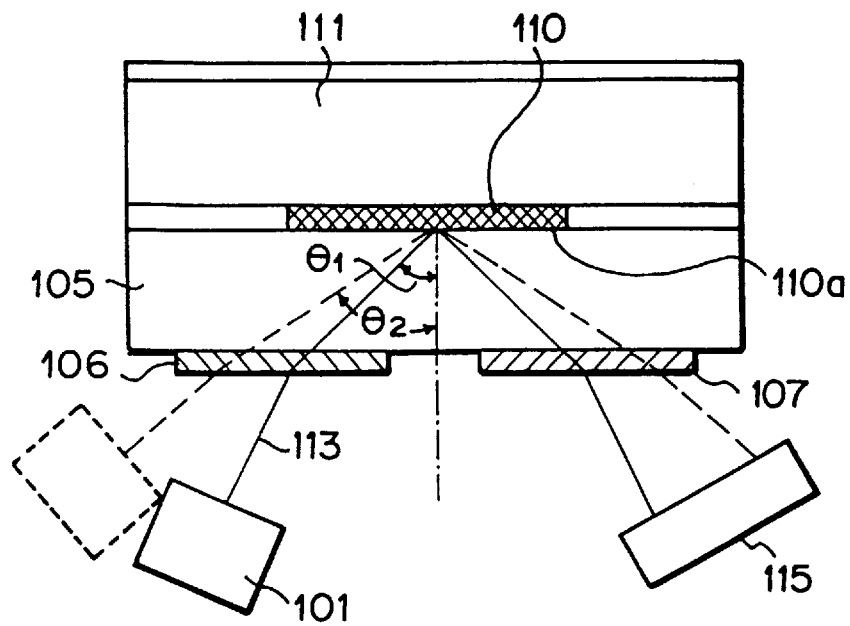
FIG. 9 is a side view showing a fifth embodiment of the surface plasmon sensor in accordance with the present invention.

FIG. 9 is a side view showing a fifth embodiment of the surface plasmon sensor in accordance with the present invention. As illustrated in FIG. 9, the surface plasmon sensor comprises a light source 101, which produces a light beam 113 and may be constituted of a semiconductor laser, or the like, and a glass substrate 105. The surface plasmon sensor also comprises a grating 106 for entry of the light beam, which is formed at a portion of one surface (the lower surface in FIG. 9) of the glass substrate 105, and a sensor means (a metal film) 110, which is formed on the other surface of the glass substrate 105 and is brought into contact with a sample 111. The grating 106 for entry of the light beam diffracts the light beam 113 and causes it to enter into the glass substrate 105. The sensor means 110 may be constituted of gold, silver, or the like. The surface plasmon sensor further comprises a grating 107 for radiation of the light beam, which is formed at a portion of the one surface (the lower surface in FIG. 9) of the glass substrate 105. The grating 107 for radiation of the light beam diffracts the light beam 113 having been totally reflected from an interface 110a between the glass substrate 105 and the metal film 110 and radiates the light beam 113 out of the glass substrate 105. The surface plasmon sensor still further comprises a photo detecting means 115 for detecting the light beam 113, which has been radiated out of the glass substrate 105.

The light source 101 is rotated by a goniometer (not shown), such that the angles of incidence of the light beam 113 upon the glass substrate 105 and upon the metal film 110 may take various values. Specifically, in the fifth embodiment of FIG. 9, the goniometer corresponds to the optical system for causing the light beam to impinge upon the substrate in the aforesaid seventh surface plasmon sensor in accordance with the present invention. As exemplified by the minimum angle of incidence $\theta_1$ and the maximum angle of incidence $\theta_2$ in FIG. 9, the light beam 113 impinges at various different angles of incidence $\theta$ upon the interface 110a between the glass substrate 105 and the metal film 110. The angles of incidence $\theta$ are set to be not smaller than the critical angle of total reflection, such that the light beam 113 may be totally reflected from the interface 110a.

The angle of reflection of the light beam 113, which is reflected from the interface 110a, changes in accordance with the change in angle of incidence. Therefore, as the photo detecting means 115, means comprising light receiving elements arrayed in the direction, along which the angle of reflection changes, is employed. By way of example, the photo detecting means 115 may be constituted of a CCD line sensor.

In lieu of the goniometer being used, various different angles of incidence may be obtained by deflecting the light beam with a galvanometer mirror, which is described in, for example, Japanese Patent Application No. 8(1996)-109367. Also, the photo detecting means 115 may be rotated by a goniometer in accordance with the change in angle of reflection due to the rotation of the light source, and the intensity of the light beam may thereby be detected.

How a sample analysis is carried out in the fifth embodiment of the surface plasmon sensor shown in FIG. 9 will be described hereinbelow. The sample 11 subjected to the analysis is located such that it may in contact with the metal film 110. The light beam 113 is set to be composed of P-polarized light component and is caused by the goniometer to enter at various different angles of incidence from the grating 106 for entry of the light beam into the glass substrate 105. The light beam 113 is diffracted by the grating 106 for entry of the light beam and is caused to impinge at angles of incidence $\theta$ upon the metal film 110. The light beam 113 is then totally reflected from the interface 110a between the metal film 110 and the glass substrate 105, diffracted by the grating 107 for radiation of the light beam, and radiated out of the glass substrate 105. The light beam 113 having thus been radiated out of the glass substrate 105 is detected by the photo detecting means 115.

A photo detection signal S obtained from each of the light receiving elements of the photo detecting means 115 represents the intensity I of the totally reflected light beam 113 with respect to each of the angles of incidence $\theta$ upon the interface 110a between the glass substrate 105 and the metal film 110. FIG. 2 approximately shows the relationship between the intensity I of the reflected light and the angles of incidence $\theta$.

The light impinging at a specific angle of incidence (a total reflection cancellation angle) $\theta_{SP}$ upon the interface 110a excites surface plasmon at an interface between the metal film 110 and the sample 111. As for the light impinging at the specific angle of incidence $\theta_{SP}$ upon the interface 110a, the intensity I of the reflected light becomes markedly low. From the photo detection signal S obtained from each of the light receiving elements of the photo detecting means 115, the total reflection cancellation angle $\theta_{SP}$ can be determined. As described above in detail, a substance to be analyzed contained in the sample 111 can be analyzed quantitatively in accordance with the value of the total reflection cancellation angle $\theta_{SP}$.

Figure 10:
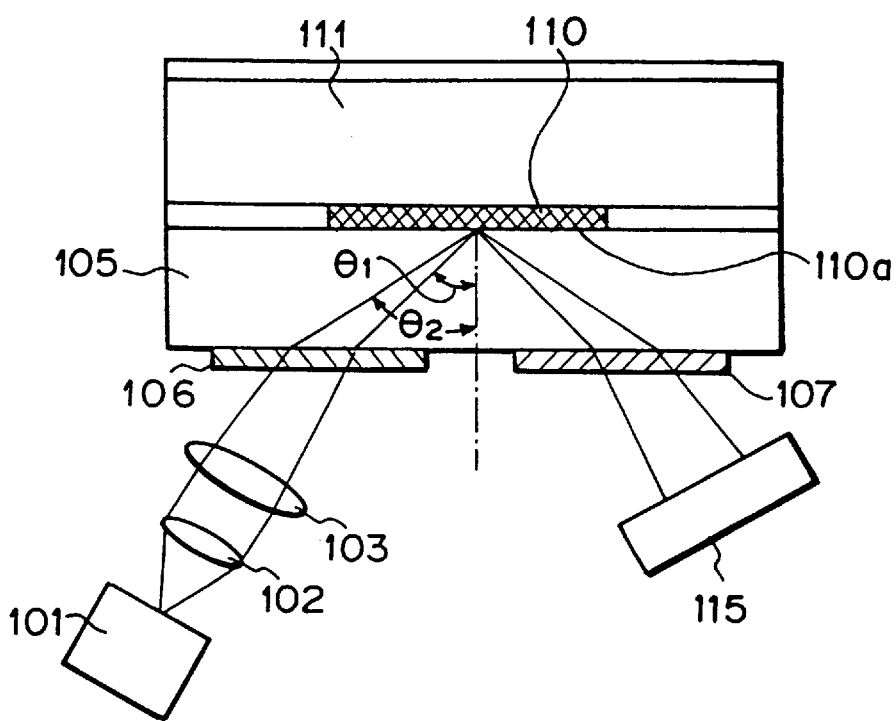
FIG. 10 is a side view showing a sixth embodiment of the surface plasmon sensor in accordance with the present invention.

As an alternative to the constitution of the fifth embodiment of FIG. 9, as illustrated in FIG. 10, a collimator lens 102 and a converging lens 103 may be employed as the optical system, and the converged light beam may be irradiated to the interface 110a. As exemplified by the minimum angle of incidence $\theta_1$ and the maximum angle of incidence $\theta_2$ in FIG. 10, the converged light beam contains components impinging at various different angles of incidence $\theta$ upon the interface 110a. Therefore, the light beam, which has been totally reflected from the interface 110a, contains the components, which have been reflected at various different angles of reflection. The intensity of the light beam having been radiated out of the glass substrate 105 is detected by the photo detecting means 115. As the photo detecting means 115, a CCD line sensor, a photodiode, a two-part photodiode as described in, for example, Japanese Patent Application No. 8(1996)-109366, a photodiode array, or the like, may be employed. As in the fourth embodiment of FIG. 9, the total reflection cancellation angle $\theta_{SP}$ can be found from the photo detection signal, and a specific substance contained in the sample 111 can be analyzed quantitatively.

In the embodiments described above, the total reflection cancellation angle $\theta_{SP}$ is obtained from the intensity of the reflected light with respect to various different angles of incidence. Alternatively, the total reflection cancellation angle $\theta_{SP}$ may be obtained by utilizing the characteristics such that the intensity of the reflected light with respect to a certain angle of incidence changes in accordance with the value of the total reflection cancellation angle $\theta_{SP}$. For example, the angle of incidence of the light beam may be set at a predetermined angle smaller than the total reflection cancellation angle $\theta_{SP}$, and the total reflection cancellation angle $\theta_{SP}$ may be obtained in accordance with the intensity of the reflected light, which is obtained at this time.

Embodiments of the evanescent ellipsosensor in accordance with the present invention will be described hereinbelow.

Figure 11:
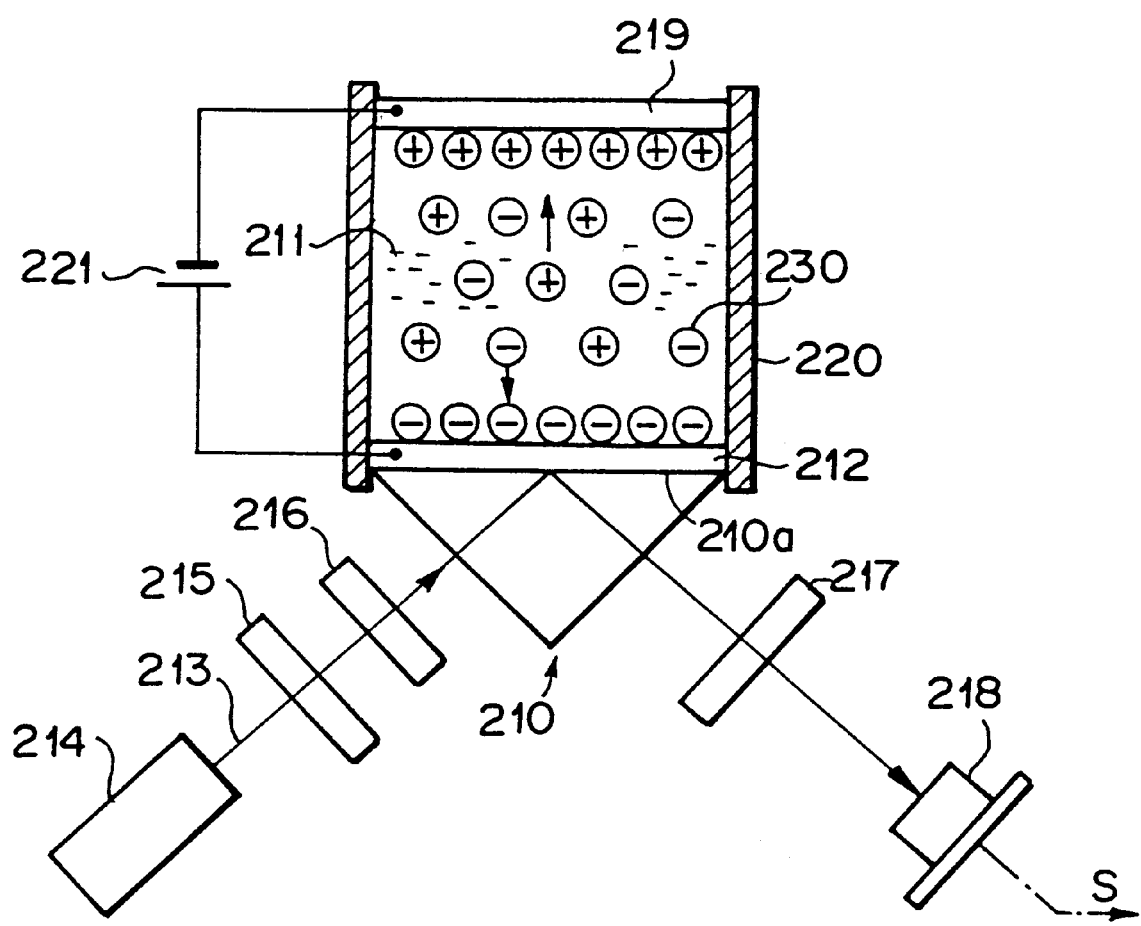
FIG. 11 is a side view showing a first embodiment of the evanescent ellipsosensor in accordance with the present invention.

FIG. 11 is a side view showing a first embodiment of the evanescent ellipsosensor in accordance with the present invention. As illustrated in FIG. 11, the evanescent ellipsosensor comprises a prism 210 having a triangular cross-section, a transparent electrode 212, which is formed on one surface (an upper surface in FIG. 11) of the prism 210 and is brought into contact with a liquid sample 211, and a light source 214, which produces a light beam 213 and may be constituted of a laser. The evanescent ellipsosensor also comprises a polarizer 215 and a quarter-wave plate 216 for controlling the condition of polarization of the light beam 213, which has been produced by the light source 214. The evanescent ellipsosensor further comprises an analyzer 217, which is located in the optical path of the light beam 213 having been totally reflected from an interface 210a between the prism 210 and the transparent electrode 212, and a photo detecting means 218 for detecting the intensity of the light beam 213 having passed through the analyzer 217.

An opposite electrode 219 is located at a position spaced an appropriate distance from the transparent electrode 212 such that it may stand facing the transparent electrode 212. The opposite electrode 219 is supported by a tube-like support member 220 having its center axis extending vertically in FIG. 11. The periphery of the region sandwiched between the transparent electrode 212 and the opposite electrode 219 is closed by the support member 220. The transparent electrode 212 and the opposite electrode 219 are respectively connected to a positive pole and a negative pole of a DC power source 221.

The beam irradiating system, which is composed of the light source 214, the polarizer 215, and the quarter-wave plate 216, is located such that the light beam 213 may impinge at an angle of incidence not smaller than the total reflection angle upon the interface 210a. Also, the polarizer 215 and the quarter-wave plate 216 convert the light beam 213 into an elliptically polarized light such that it may constitute a linearly polarized light after being totally reflected from the interface 210a. The analyzer 217 is rotated around the optical axis.

How a sample analysis is carried out in the evanescent ellipsosensor having the constitution described above will be described hereinbelow. The region between the transparent electrode 212 and the opposite electrode 219 is filled with the liquid sample 211, which contains an anionic substance to be analyzed 230. Also, the DC power source 221 applies a DC voltage across the transparent electrode 212 and the opposite electrode 219. The light beam 213 having been converted into the elliptically polarized light is irradiated toward the transparent electrode 212. The light beam 213 is totally reflected from the interface 210a between the transparent electrode 212 and the prism 210, and the reflected light beam 213 is detected by the photo detecting means 218.

When the light beam 213 is totally reflected from the interface 210a, a difference in phase between the P-polarized light component (i.e., the polarized light component having a plane of vibration parallel to the interface 210a) and the S-polarized light component (i.e., the polarized light component having a plane of vibration normal to the interface 210a) varies for the incident light and the reflected light. As described above, the change in difference in phase, i.e. the change in condition of polarization, due to the total reflection reflects the physical properties and the total amount of the substance to be analyzed 230, which adheres to the transparent electrode 212. Therefore, the analyzer 217 is rotated such that an output S of the photo detecting means 218 may become smallest. At this time, from the rotation angle of the analyzer 217, the change in condition of polarization due to the total reflection, and consequently the physical properties and the total amount of the substance to be analyzed 230, can be determined.

Also, since the DC voltage is applied across the transparent electrode 212 and the opposite electrode 219, which are connected to the DC power source 221, the anionic substance to be analyzed 230, which is contained in the liquid sample 211, is electro-deposited on the transparent electrode 212. Therefore, the concentration of the substance to be analyzed 230 becomes high at the portion of the liquid sample 211, which portion is in contact with the transparent electrode 212, and the substance to be analyzed 230 can be analyzed quickly and with a high sensitivity. As the anionic substance to be analyzed 230, human serum transferrin dissolved in sodium hydroxide, or the like, may be mentioned.

In cases where the substance to be analyzed 230, which is contained in the liquid sample 211, is detected by the utilization of an antigen-antibody reaction, it is often desired that the change in condition of polarization of the light beam 213 can be detected on the real time basis as time passes while the antigen-antibody reaction is proceeding. With the first embodiment of the evanescent ellipsosensor in accordance with the present invention, wherein the substance to be analyzed 230 can be detected quickly as described above, the real time detection can be completed quickly.

In the first embodiment of the evanescent ellipsosensor in accordance with the present invention, the change in condition of polarization of the light beam 213 due to the total reflection is detected with the analyzer 217, which rotates, and the photo detecting means 218. Alternatively, the change in condition of polarization of the light beam 213 may be detected with one of other known techniques, for example, a technique for utilizing a photoelastic modulator (PEM).

Figure 12:
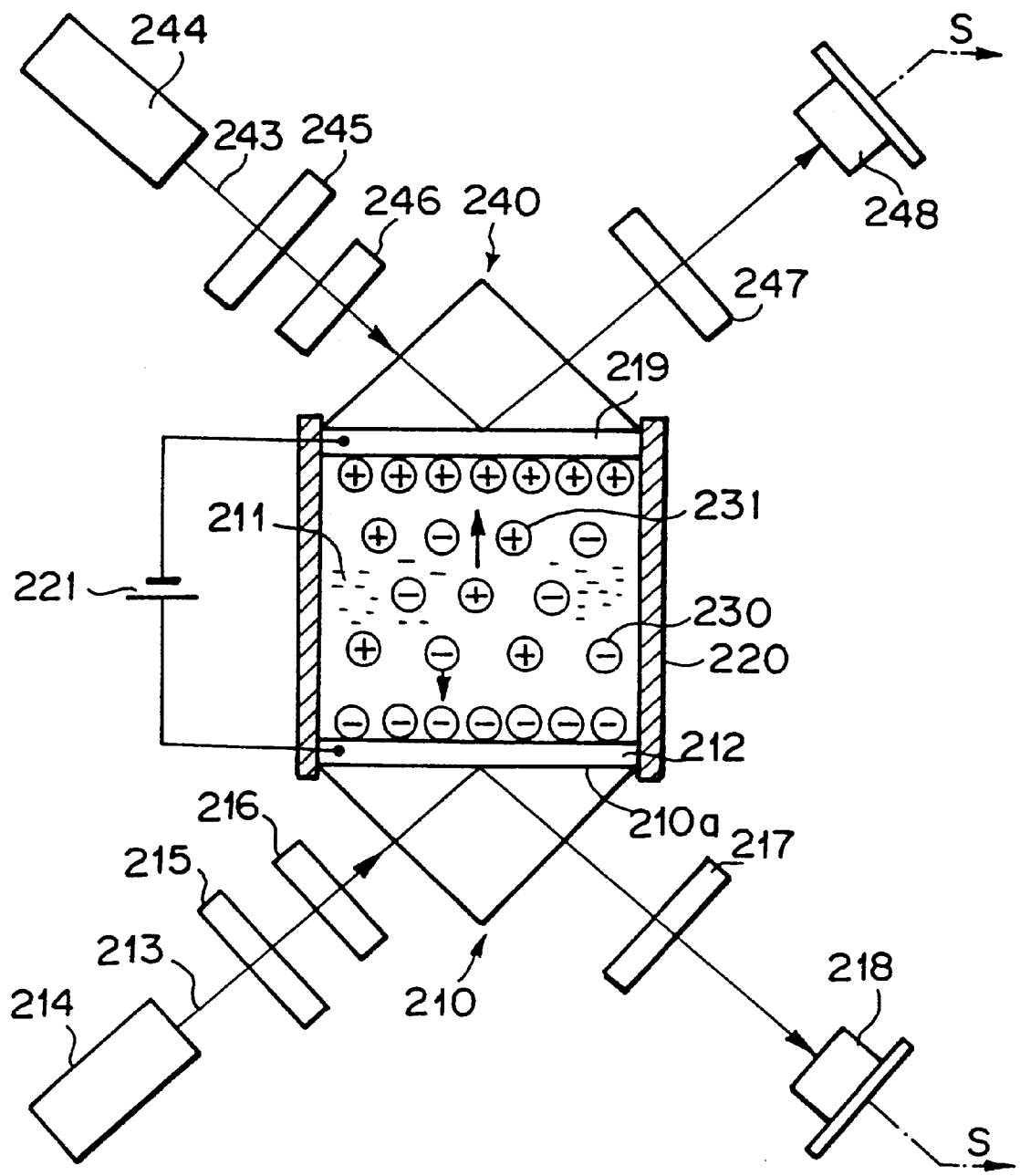
FIG. 12 is a side view showing a second embodiment of the evanescent ellipsosensor in accordance with the present invention.

A second embodiment of the evanescent ellipsosensor in accordance with the present invention will be described hereinbelow with reference to FIG. 12. In FIG. 12, similar elements are numbered with the same reference numerals with respect to FIG. 11.

The second embodiment of the evanescent ellipsosensor shown in FIG. 12 is basically similar to the first embodiment of FIG. 11, except that the second embodiment further comprises a second prism 240, a second light source 244 for producing a second light beam 243, a second polarizer 245, a second quarter-wave plate 246, a second analyzer 247, and a second photo detecting means 248. In this case, as the opposite electrode 219, a transparent electrode is employed.

The elements newly added to the second embodiment of the evanescent ellipsosensor in accordance with the present invention constitute another evanescent ellipsosensor by utilizing the opposite electrode 219, which is constituted of the transparent electrode, in the same manner as that of the transparent electrode 212. Specifically, the second prism 240, the second light source 244, the second polarizer 245, the second quarter-wave plate 246, the second analyzer 247, and the second photo detecting means 248 respectively have the same actions as those of the prism 210, the light source 214, the polarizer 215, the quarter-wave plate 216, the analyzer 217, and the photo detecting means 218.

In the second embodiment of the evanescent ellipsosensor shown in FIG. 12, the analysis of the anionic substance to be analyzed 230, which is contained in the liquid sample 211, is carried out in the same manner as that described above. Also, in the second embodiment of FIG. 12, a cationic substance to be analyzed 231, which is contained in the liquid sample 211, is electro-deposited on the opposite electrode 219. Therefore, with the second prism 240, the second light source 244, the second polarizer 245, the second quarter-wave plate 246, the second analyzer 247, and the second photo detecting means 248, an analysis of the substance to be analyzed 231 can be carried out in the same manner.

In such cases, the concentration of the substance to be analyzed 231 becomes high at the portion of the liquid sample 211, which portion is in contact with the opposite electrode 219, and the substance to be analyzed 231 can be analyzed quickly and with a high sensitivity.

Embodiments of the electrophoresis sensor in accordance with the present invention will be described hereinbelow.

Figure 13:
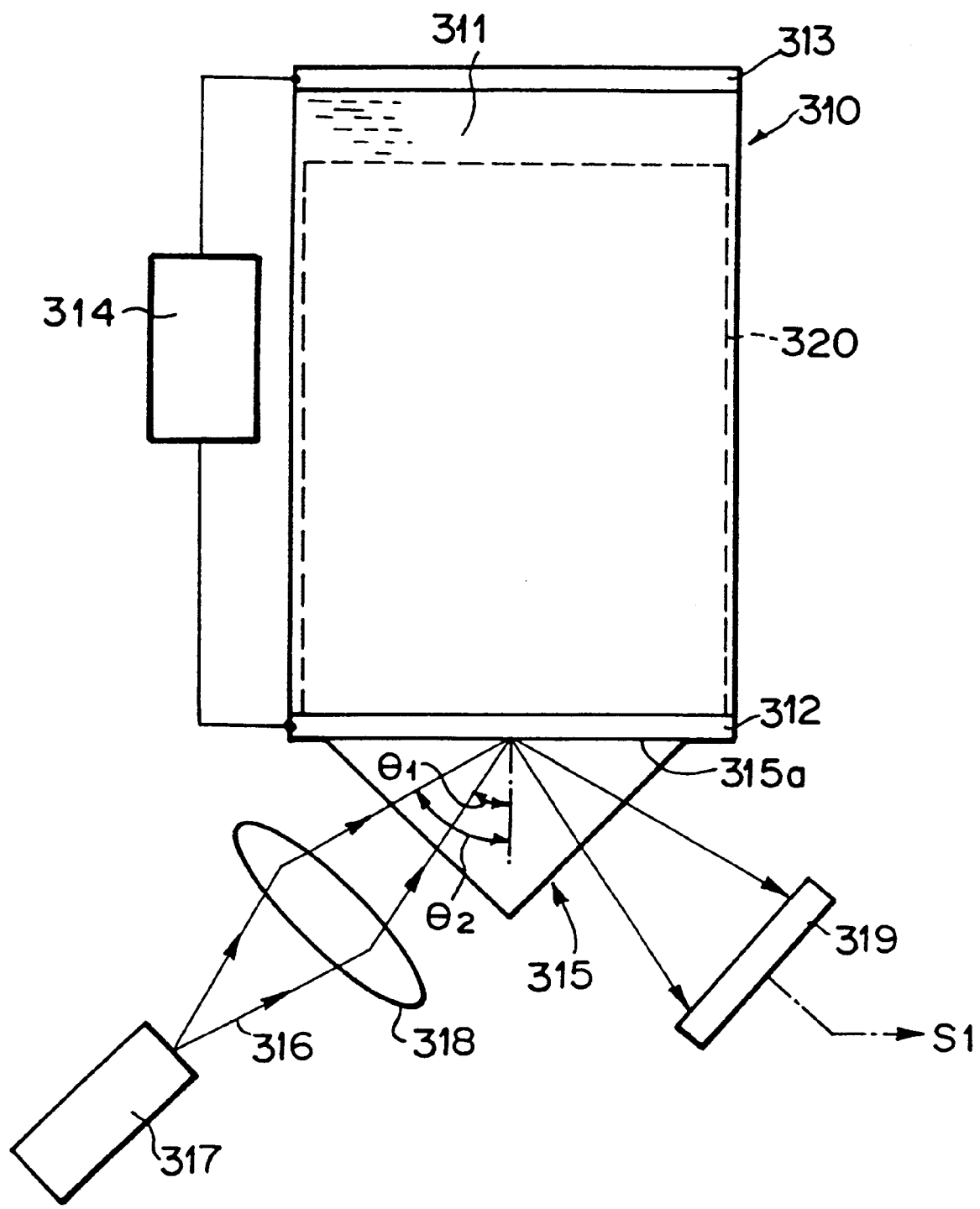
FIG. 13 is a side view showing a first embodiment of the electrophoresis sensor in accordance with the present invention.

FIG. 13 is a side view showing a first embodiment of the electrophoresis sensor in accordance with the present invention. As illustrated in FIG. 13, the electrophoresis sensor comprises a heat-insulating vessel 310 filled with a liquid sample 311, a first electrode 312 which is located at the bottom of the heat-insulating vessel 310 such that it may be in contact with the liquid sample 311, and a second electrode 313 which is located at the top of the heat-insulating vessel 310 such that it may be in contact with the liquid sample 311. The electrophoresis sensor also comprises a DC power source 314 for applying a DC voltage across the first electrode 312 and the second electrode 313. As the first electrode 312, by way of example, a metal film constituted of gold, silver, or the like, is employed.

The electrophoresis sensor further comprises a prism 315, which has a triangular prism-like shape and is brought into contact with the first electrode 312 from below (i.e., from the exterior of the heat-insulating vessel 310. The electrophoresis sensor still further comprises a light source 317, which produces a light beam 316 and may be constituted of a semiconductor laser, or the like, and a cylindrical lens 318 for converging the light beam 316, which has been radiated in a divergent light condition from the light source 317, only in a plane normal to the major axis of the prism 315 (i.e., a plane parallel to the plane of the sheet of FIG. 13). The electrophoresis sensor also comprises a photo detecting means 319 for detecting an intensity of the light beam 316, which has been totally reflected from an interface 315a between the prism 315 and the first electrode 312.

The light beam 316 is converged in the manner described above by the action of the cylindrical lens 318. Therefore, as exemplified by the minimum angle of incidence $\theta_1$ and the maximum angle of incidence $\theta_2$ in FIG. 13, the light beam 316 contains components impinging at various different angles of incidence $\theta$ upon the interface 315a. The angles of incidence $\theta$ are set to be not smaller than the total reflection angle. As a result, the light beam 316 is totally reflected from the interface 315a, and the reflected light beam 316 contains the components, which have been reflected at various different angles of reflection.

As the photo detecting means 319, means having a light receiving section, which extends in the direction that is capable of receiving all of the components of the light beam 316 having been reflected at different angles of reflection in the manner described above, is employed. The photo detecting means 319 may be constituted of a CCD line sensor, or the like. A photo detection signal S1 is obtained from each of light receiving elements of the photo detecting means 319. Therefore, the photo detection signal S1 represents the intensity of the light beam 316 with respect to each of the various different angles of reflection (i.e., with respect to each of the various different angles of incidence).

How a sample analysis is carried out in the first embodiment of the electrophoresis sensor having the constitution described above will be described hereinbelow. A gel sheet 320, which is constituted of a polyacrylamide gel, or the like, and serves as an electrophoresis medium, is located in the heat-insulating vessel 310 such that one end (the lower end in FIG. 13) of the gel sheet 320 may be in contact with the first electrode 312. Also, the heat-insulating vessel 310 is filled with the liquid sample 311. The DC power source 314 applies the DC voltage across the first electrode 312 and the second electrode 313. The light beam 316 is converged by the action of the cylindrical lens 318 in the manner described above and is irradiated toward the first electrode 312. The light beam 316 is totally reflected from the interface 315a between the first electrode 312 and the prism 315, and the reflected light beam 316 is detected by the photo detecting means 319.

As described above, the photo detection signal S1 obtained from each of the light receiving elements of the photo detecting means 319 represents the intensity I of the totally reflected light beam 316 with respect to each of the angles of incidence $\theta$. FIG. 2 approximately shows the relationship between the intensity I of the reflected light and the angles of incidence $\theta$.

The light impinging at a specific angle of incidence $\theta_{SP}$ upon the interface 315a excites surface plasmon at an interface between the first electrode 312 and the liquid sample 311. As for the light impinging at the specific angle of incidence $\theta_{SP}$ upon the interface 315a, the intensity I of the reflected light becomes markedly low. From the photo detection signal S1 obtained from each of the light receiving elements of the photo detecting means 319, the specific angle of incidence $\theta_{SP}$ can be determined. As described above in detail, a substance to be analyzed, which is contained in the liquid sample 311, can be analyzed quantitatively in accordance with the value of $\theta_{SP}$.

Also, since the DC voltage is applied across the first electrode 312 and the second electrode 313, which are connected to the DC power source 314, a plurality of substances contained in the liquid sample 311 migrate through the gel sheet 320 and arrive one after another at the first electrode 312. At this time, the plurality of the substances arrive at the first electrode 312 at different time intervals due to differences in migration speed. Specifically, the substance, which is quantitatively analyzed in accordance with the photo detection signal S1, is each of the substances having thus migrated through the gel sheet 320. The substances are detected separately from one another in accordance with the photo detection signal S1, the value of which changes with the passage of time.

In the first embodiment of the electrophoresis sensor in accordance with the present invention, in order for the various different angles of incidence $\theta$ to be obtained, the light beam 316 having a comparatively large beam diameter is irradiated such that it may be converged on the interface 315a. Alternatively, various different angles of incidence $\theta$ may be obtained by deflecting a light beam having a comparatively small beam diameter.

Figure 14:
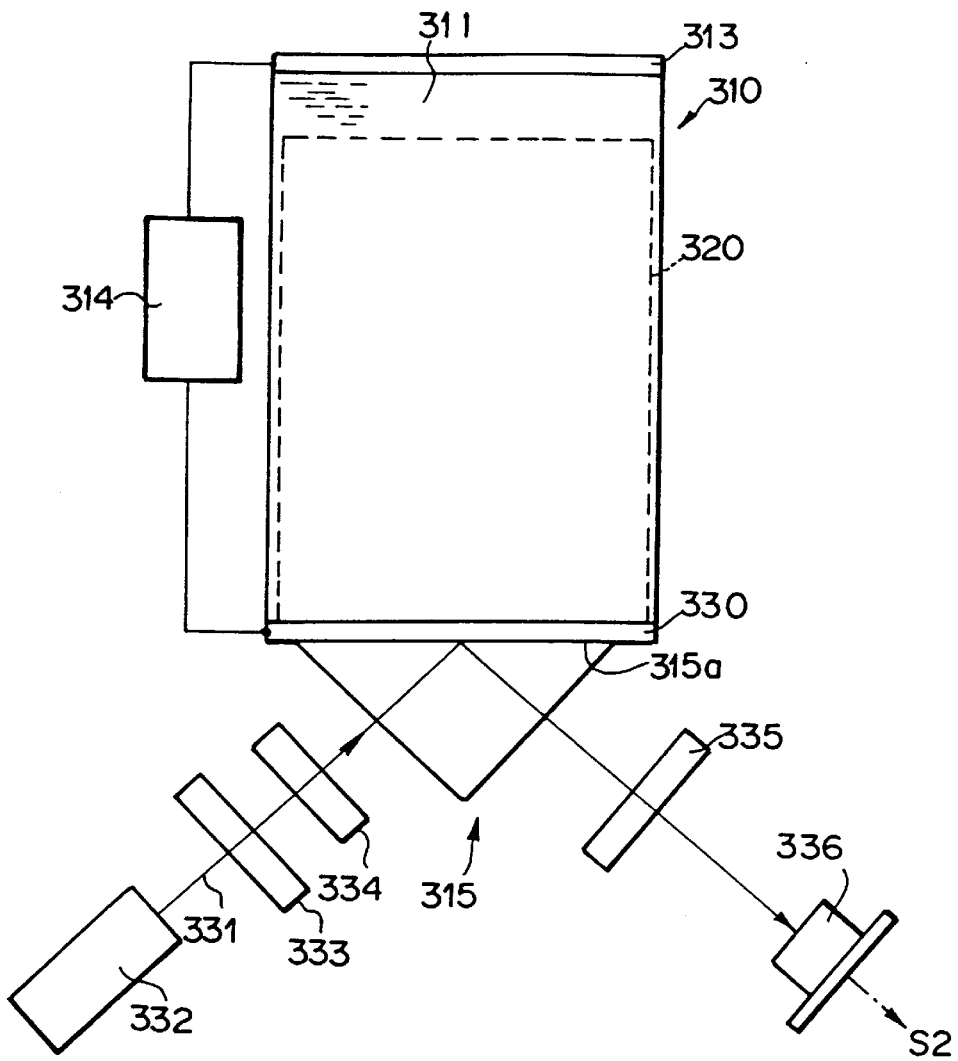
FIG. 14 is a side view showing a second embodiment of the electrophoresis sensor in accordance with the present invention.

A second embodiment of the electrophoresis sensor in accordance with the present invention will be described hereinbelow with reference to FIG. 14. In FIG. 14 and in FIGS. 16, 17, and 18, similar elements are numbered with the same reference numerals with respect to FIG. 13.

In the second embodiment of the electrophoresis sensor shown in FIG. 14, the constitution for electrophoresis is basically similar to that in the first embodiment of FIG. 13, and only the sensor section for light is different from that in the first embodiment. Specifically, the electrophoresis sensor shown in FIG. 14 comprises the prism 315 which is of the same type as that in the first embodiment shown in FIG. 13, a transparent first electrode 330, which is formed on one surface (an upper surface in FIG. 14) of the prism 315 and is brought into contact with the liquid sample 311, and a light source 332, which produces a light beam 331 and may be constituted of a laser. The electrophoresis sensor also comprises a polarizer 333 and a quarter-wave plate 334 for controlling the condition of polarization of the light beam 331, which has been produced by the light source 332. The electrophoresis sensor further comprises an analyzer 335, which is located in the optical path of the light beam 331 having been totally reflected from the interface 315a between the prism 315 and the transparent first electrode 330, and a photo detecting means 336 for detecting the intensity of the light beam 331 having passed through the analyzer 335.

The beam irradiating system, which is composed of the light source 332, the polarizer 333, and the quarter-wave plate 334, is located such that the light beam 331 may impinge at an angle of incidence not smaller than the total reflection angle upon the interface 315a. Also, the polarizer 333 and the quarter-wave plate 334 convert the light beam 331 into a circularly polarized light immediately before the light beam 331 impinges upon the interface 315a. The analyzer 335 is rotated around the optical axis.

How a sample analysis is carried out in the second embodiment of the electrophoresis sensor having the constitution described above will be described hereinbelow. The aforesaid gel sheet 320 is located in the heat-insulating vessel 310 such that one end (the lower end in FIG. 14) of the gel sheet 320 may be in contact with the first electrode 330. Also, the heat-insulating vessel 310 is filled with the liquid sample 311. The DC power source 314 applies the DC voltage across the first electrode 330 and the second electrode 313. The light beam 331, which has been converted into the circularly polarized light, is irradiated toward the first electrode 330. The light beam 331 is totally reflected from the interface 315a between the first electrode 330 and the prism 315, and the reflected light beam 331 is detected by the photo detecting means 336.

When the light beam 331 is totally reflected from the interface 315a, a difference in phase between the P-polarized light component (i.e., the polarized light component having a plane of vibration parallel to the interface 315a) and the S-polarized light component (i.e., the polarized light component having a plane of vibration normal to the interface 315a) varies for the incident light and the reflected light. The change in difference in phase, i.e. the change in condition of polarization, due to the total reflection reflects the physical properties and the total amount of the substance to be analyzed, which adheres to the first electrode 330. Therefore, ellipticity of the polarized light is determined from an output S2 of the photo detecting means 336, and a shift from the circular polarization is thus investigated. In this manner, the change in condition of polarization due to the total reflection, and consequently the physical properties and the total amount of the substance to be analyzed, can be determined.

Also, since the DC voltage is applied across the first electrode 330 and the second electrode 313, the plurality of the substances contained in the liquid sample 311 migrate through the gel sheet 320 and arrive one after another at the first electrode 330. At this time, the plurality of the substances arrive at the first electrode 330 at different time intervals due to differences in migration speed. Therefore, the substances can be detected temporally separately from one another.

Figure 15:
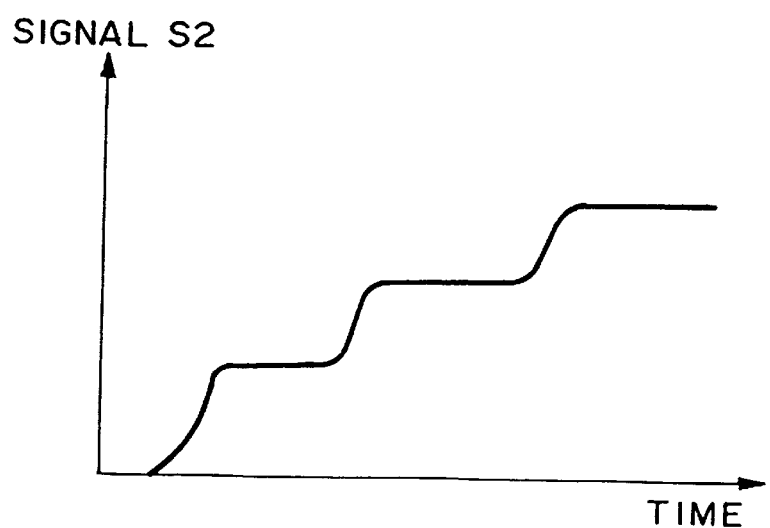
FIG. 15 is a graph showing how a photo detection signal changes in the second embodiment of the electrophoresis sensor shown in FIG. 14.

In the second embodiment of the electrophoresis sensor in accordance with the present invention, the change in condition of polarization of the light beam 331 due to the total reflection is detected with the analyzer 335, which rotates, and the photo detecting means 336. Alternatively, the change in condition of polarization of the light beam 331 may be detected with one of other known techniques. For example, in cases where the analyzer 335 is kept stationary without being rotated, the photo detection signal S2 changes moment by moment in accordance with the change in condition of polarization. Therefore, the change in condition of polarization can be detected in the real time basis in accordance with the value of the photo detection signal S2. FIG. 15 shows how the photo detection signal S2 changes with the passage of time.

One example of the separative detection of substances is the separative detection of collagen polypeptide chains. Molecular weights of an $\alpha$-chain, a $\beta$-chain, and a $\gamma$-chain in collagen are respectively 96,000, 192,000, and 288,000. When a voltage is applied for the detection of these substances such that the first electrode 330 may serve as a positive electrode, the respective substances migrate toward the first electrode 330. A substance having a small molecular weight migrates at a high migration speed. Therefore, $\alpha$-chain, the $\beta$-chain, and the $\gamma$-chain arrive in this order at the first electrode 330. When each of these substances arrives at the first electrode 330, the dielectric constant (the refractive index) in the vicinity of the surface of the first electrode 330 changes in accordance with each substance, and the aforesaid condition of polarization is thereby caused to change. As described above, the change in condition of polarization is detected as a change in photo detection signal S2.

Figure 16:
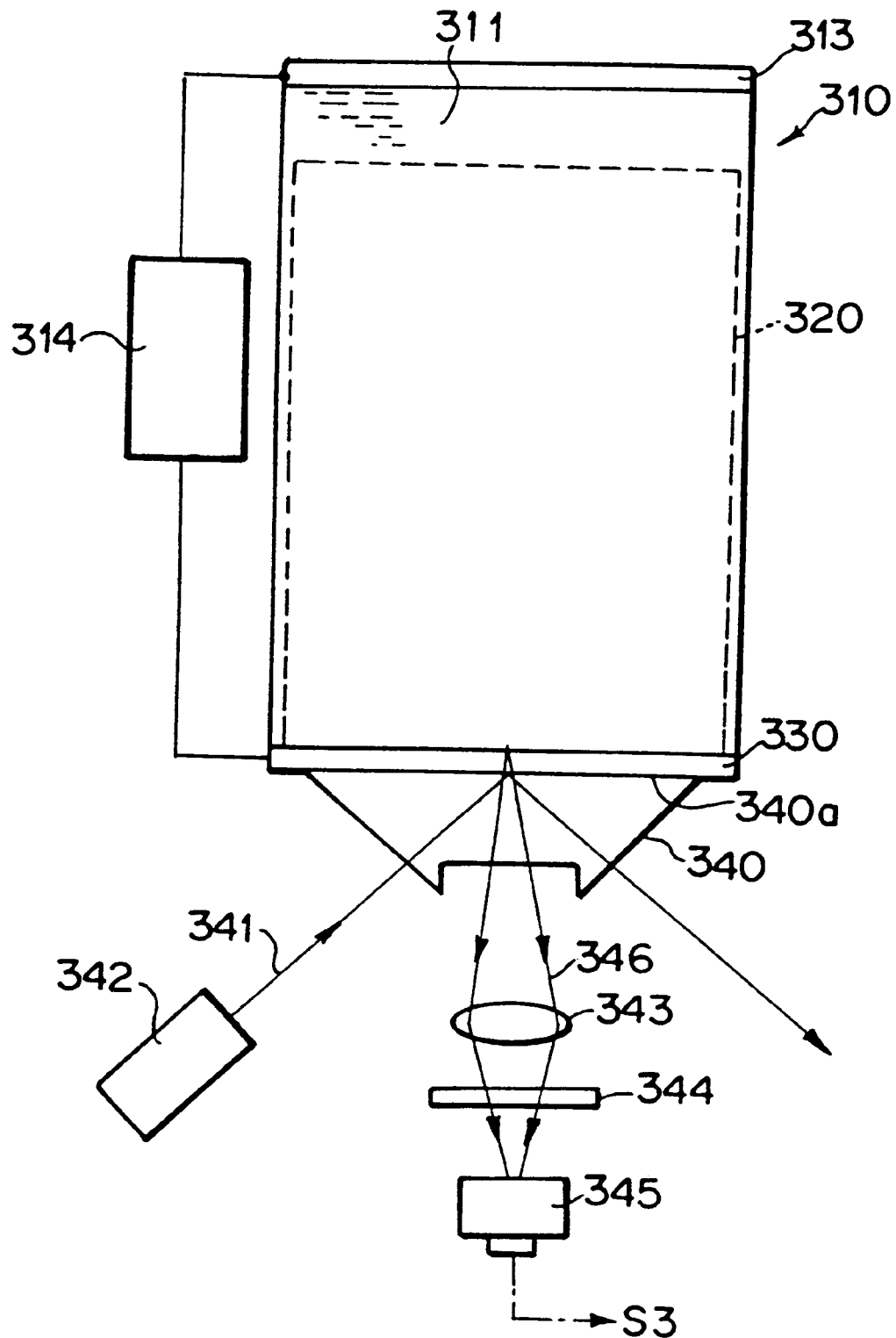
FIG. 16 is a side view showing a third embodiment of the electrophoresis sensor in accordance with the present invention.

A third embodiment of the electrophoresis sensor in accordance with the present invention will be described hereinbelow with reference to FIG. 16. In the third embodiment of the electrophoresis sensor shown in FIG. 16, the constitution for electrophoresis is basically similar to that in the first embodiment of FIG. 13, and only the sensor section for light is different from that in the first embodiment. Specifically, the electrophoresis sensor shown in FIG. 16 comprises a prism 340, which has an approximately trapezoidal cross-section and is located such that it may be in contact with the transparent first electrode 330, and a light source 342, which irradiates a light beam 341 to the prism 340 and may be constituted of a laser. The electrophoresis sensor also comprises a converging lens 343 for converging fluorescence 346, which will be described later, and a wavelength filter 344 for selectively transmitting the fluorescence 346, and a photodetector 345 for detecting the fluorescence 346. The light source 342 is located such that the light beam 341 having been produced by it may be totally reflected from an interface 340a between the prism 340 and the first electrode 330.

How a sample analysis is carried out in the third embodiment of the electrophoresis sensor having the constitution described above will be described hereinbelow. The aforesaid gel sheet 320 is located in the heat-insulating vessel 310 such that one end (the lower end in FIG. 16) of the gel sheet 320 may be in contact with the first electrode 330. Also, the heat-insulating vessel 310 is filled with the liquid sample 311. A substance to be detected, which is contained in the liquid sample 311, is labeled with a coloring matter which is one kind of fluorescent substances. The DC power source 314 applies the DC voltage across the first electrode 330 and the second electrode 313. Also, the light beam 341 is irradiated toward the first electrode 330.

When the light beam 341 is totally reflected from the interface 340a, an evanescent wave leaks from the interface 340a toward the first electrode 330. At this time, if the substance, which is labeled with the coloring matter and is contained in the liquid sample 311, has arrived at the first electrode 330, the coloring matter will be excited with the evanescent wave and will generate the fluorescence 346. The fluorescence 346 is converged by the converging lens 343, guided to the photodetector 345, and detected by the photodetector 345. Thus in this embodiment, the substance, which is labeled with the coloring matter and is contained in the liquid sample 311, can be detected in accordance with a photo detection signal S3 obtained from the photodetector 345.

In the third embodiment of the electrophoresis sensor, since the DC voltage is applied across the first electrode 330 and the second electrode 313, the plurality of the substances contained in the liquid sample 311 migrate through the gel sheet 320 and arrive one after another at the first electrode 330. At this time, the plurality of the substances arrive at the first electrode 330 at different time intervals due to differences in migration speed. Therefore, the substances can be detected temporally separately from one another.

A fourth embodiment of the electrophoresis sensor in accordance with the present invention will be described hereinbelow with reference to FIG. 17. In the fourth embodiment of the electrophoresis sensor shown in FIG. 17, the sensor section for light, which is shown in FIG. 13, is added to the constitution shown in FIG. 16.

Figure 17:
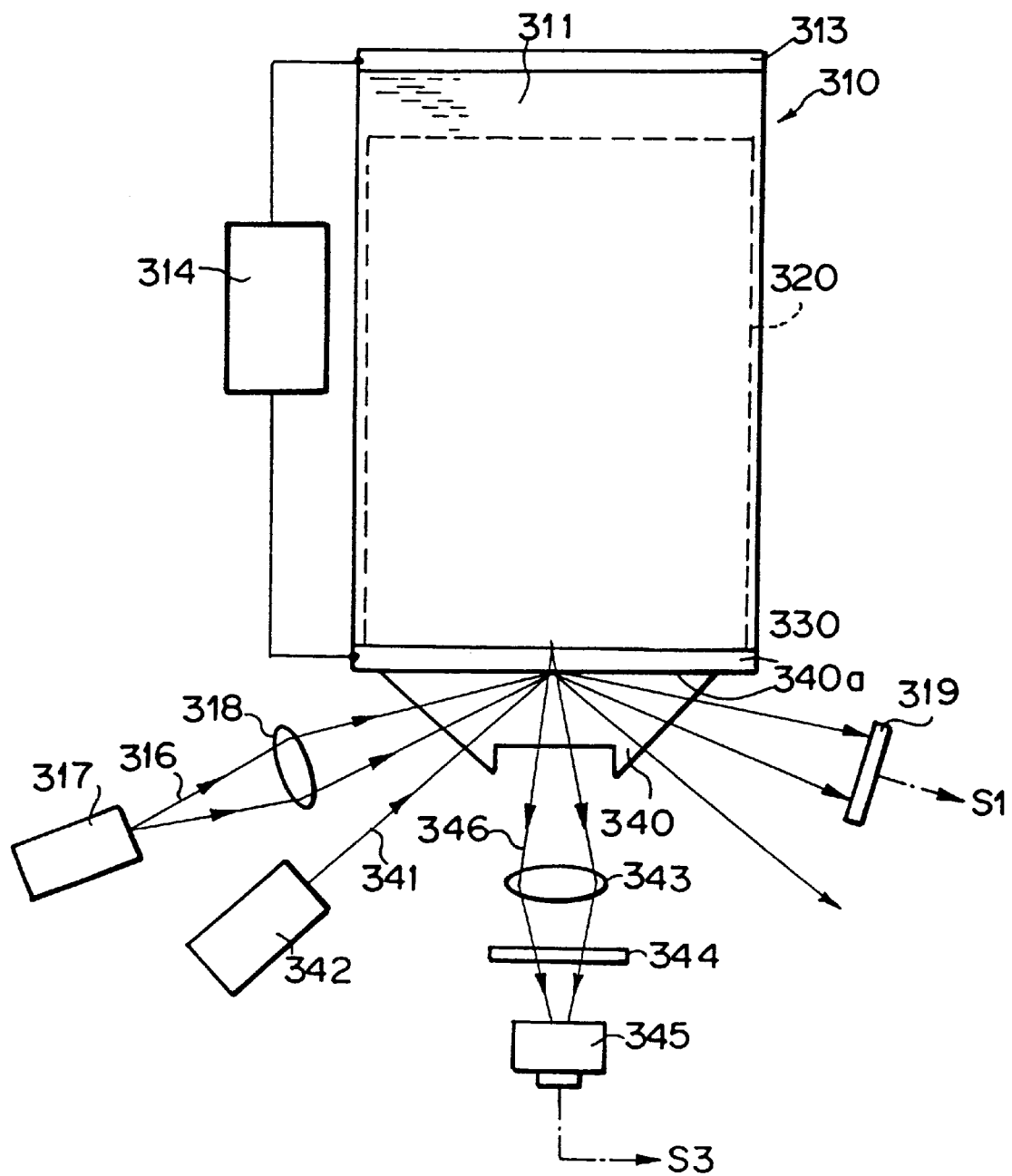
FIG. 17 is a side view showing a fourth embodiment of the electrophoresis sensor in accordance with the present invention.

When a plurality of substances, which are contained in the liquid sample 311, are to be detected separately from one another with the electrophoresis sensor of FIG. 17, only a specific substance is labeled with a coloring matter. All of the plurality of the substances are detected with the sensor section utilizing the surface plasmon (the same sensor section as that shown in FIG. 13). Of the substances, the substance labeled with the coloring matter can also be detected with fluorescence observation. Therefore, in cases where a known specific substance is labeled with the coloring matter and is utilized as a reference sample, a reference signal can be obtained from the fluorescence detection signal S3, and the other substances can be analyzed in accordance with the photo detection signal S1.

A fifth embodiment of the electrophoresis sensor in accordance with the present invention will be described hereinbelow with reference to FIG. 18. In the fifth embodiment of the electrophoresis sensor shown in FIG. 18, the sensor section for light, which is shown in FIG. 14, is added to the constitution shown in FIG. 16.

Figure 18:
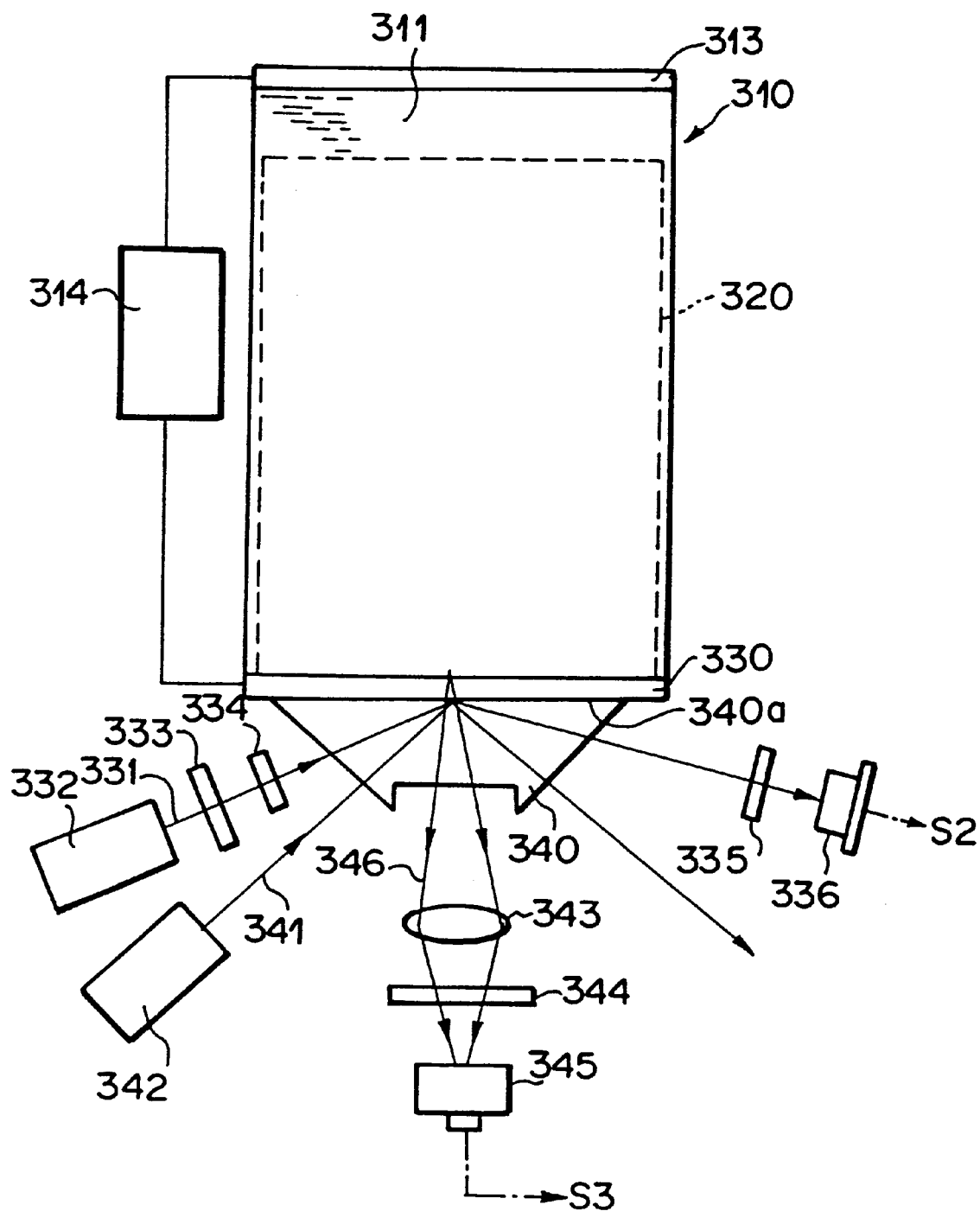
FIG. 18 is a side view showing a fifth embodiment of the electrophoresis sensor in accordance with the present invention.

When a plurality of substances, which are contained in the liquid sample 311, are to be detected separately from one another with the electrophoresis sensor of FIG. 18, a known specific substance is labeled with a coloring matter and is utilized as a reference sample. Therefore, as in the electrophoresis sensor of FIG. 17, a reference signal can be obtained from the fluorescence detection signal S3, and the other substances can be analyzed in accordance with the photo detection signal S2.

What is claimed is:

1. An electrophoresis sensor, comprising:
   i) an electrophoresis medium impregnated with a sample containing a substance;
   ii) a first electrode having a first surface contacting said electrophoresis medium;
   iii) a second electrode opposing said first electrode such that said electrophoresis medium interposes therebetween;
   iv) means for applying a DC voltage across said first electrode and said second electrode, the DC voltage causing the substance contained in the sample to migrate toward said first electrode;
   v) a prism contacting a second surface of said first electrode, said second surface facing away from said electrophoresis medium;
   vi) a beam irradiating system for causing a light beam to pass through said prism and impinge upon an interface between said prism and said first electrodes such that various angels of incidence are obtained with respect to said interface; and
   vii) a photo detecting means for detecting an intensity of the light beam, which has been totally reflected from said interface, with respect to each of the various angles of incidence.

2. An electrophoresis sensor according to claim 1, wherein said electrophoresis medium provides a sieving effect to determine the relative mobility of the substance.

3. An electrophoresis sensor, comprising:
   i) an electrophoresis medium impregnated with a sample containing a substance;
   ii) a first electrode, which is transparent, having a first surface contacting said electrophoresis medium;
   iii) a second electrode opposing said first electrode, such that said electrophoresis medium interposes therebetween;

iv) means for applying a DC voltage across said first electrode and said second electrode, the DC voltage causing the substance contained in the sample to migrate toward said first electrode;

v) a prism contacting a second surface of said first electrode, said second surface facing away from said electrophoresis medium;

vi) a beam irradiating system for irradiating a light beam in a predetermined condition of polarization, such that the light beam enters said prism and is totally reflected from an interface between said prism and said first electrode; and vii) means for detecting a change in the condition of polarization of the light beam, after the light beam is totally reflected.

4. An electrophoresis sensor according to claim 3, wherein said electrophoresis medium provides a sieving effect to determine the relative mobility of the substance.

5. An electrophoresis sensor, comprising:

i) an electrophoresis medium impregnated with a sample containing a first substance labeled with a fluorescent substance;

ii) a first electrode, which is transparent, having a first surface contacting said electrophoresis medium;

iii) a second electrode opposing said first electrode, such that said electrophoresis medium interposes therebetween;

iv) means for applying a DC voltage across said first electrode and said second electrode, the DC voltage causing the first substance contained in the sample to migrate toward said first electrode;

v) a prism contacting a second surface of said first electrode, said second surface facing away from said electrophoresis medium;

vi) a beam irradiating system for irradiating a light beam, such that the light beam enters said prism and is totally reflected from an interface between said prism and said first electrode; and vii) means for detecting fluorescence produced by the fluorescent substance when excited with an evanescent wave leaked from said interface.

6. An electrophoresis sensor according to claim 5, wherein said electrophoresis medium provides a sieving effect to determine the relative mobility of the first substance.

* * * * *